United States Patent [19]

Reiser et al.

[11] 4,315,764

[45] Feb. 16, 1982

[54] 1-ALLYLTRIAZOLE DERIVATIVES, PROCESSES FOR THEIR PREPARATION AND THEIR USE AS PLANT PROTECTION AGENTS

[75] Inventors: Wolf Reiser; Wilfried Draber; Karl H. Büchel, all of Wuppertal; Klaus Lürssen, Bergisch-Gladbach; Paul-Ernst Frohberger, Leverkusen; Volker Paul, Solingen, all of Fed. Rep. of Germany

[73] Assignee: Bayer Aktiengesellschaft, Leverkusen, Fed. Rep. of Germany

[21] Appl. No.: 118,335

[22] Filed: Feb. 4, 1980

[30] Foreign Application Priority Data

Feb. 16, 1979 [DE] Fed. Rep. of Germany ....... 2905981

[51] Int. Cl.[3] .................... A01N 43/64; C07D 249/08

[52] U.S. Cl. .......................................... 71/76; 71/74; 71/78; 71/92; 424/245; 424/269; 542/429; 542/470; 548/101; 548/262; 260/464; 568/425; 568/446; 568/447; 568/448; 568/495

[58] Field of Search ................ 542/429, 470; 548/262; 424/245, 269; 71/74, 78, 92, 76

[56] References Cited

U.S. PATENT DOCUMENTS

| | | | |
|---|---|---|---|
| 4,067,989 | 1/1978 | Shephard et al. | 424/273 R |
| 4,086,351 | 4/1978 | Balasubramanyan et al. | 424/269 |
| 4,104,399 | 8/1978 | Pommer et al. | 424/269 |
| 4,182,862 | 1/1980 | Chan | 548/262 |
| 4,203,995 | 5/1980 | Funaki | 424/273 R |

FOREIGN PATENT DOCUMENTS

| | | | |
|---|---|---|---|
| 3884 | 2/1978 | European Pat. Off. | 548/262 |
| 2645617 | 4/1977 | Fed. Rep. of Germany . | |
| 2737489 | 2/1978 | Fed. Rep. of Germany | 548/341 |
| 2652313 | 5/1978 | Fed. Rep. of Germany . | |

*Primary Examiner*—Alton D. Rollins

*Attorney, Agent, or Firm*—Sprung, Felfe, Horn, Lynch & Kramer

[57] ABSTRACT

1-Allyl-triazole derivatives of the formula

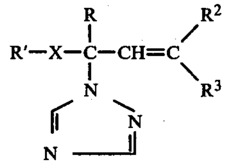

in which

R represents hydrogen, alkyl or optionally substituted aralkyl, $R^1$ represents optionally substituted alkyl, cycloalkyl or optionally substituted aryl, $R^2$ represents alkyl and $R^3$ represents alkyl, cycloalkyl, optionally substituted cycloalkenyl, alkenyl or optionally substituted aryl, or $R^2$ and $R^3$, together with the carbon atom to which they are bonded, represent optionally substituted cycloalkenyl or cycloalkyl X represent the group

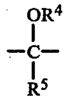

or the keto group, $R^4$ represents hydrogen, alkyl, optionally substituted aralkyl, acyl or optionally substituted carbamoyl and $R^5$ represents hydrogen, alkyl or optionally substituted aralkyl, or acid addition salts or metal salt complexes thereof are characterized by fungicidal and plant growth regulatory activity.

7 Claims, No Drawings

1-ALLYLTRIAZOLE DERIVATIVES, PROCESSES FOR THEIR PREPARATION AND THEIR USE AS PLANT PROTECTION AGENTS

The present invention relates to certain new 1-allyltriazole derivatives, to a process for their preparation and to their use as plant growth regulators and fungicides.

It has already been disclosed that certain acylated and carbamoylated derivatives of 3,3-dimethyl-1-phenoxy-1-triazolyl-butan-2-ols substituted in the phenyl part have a good fungicidal activity (see DE-OS (German Published Specification) No. 2,600,799), as have certain 4,4-dimethyl-1-phenyl-2-triazolyl-pentan-3-ones substituted in the phenyl part, for example 1-(4-chlorophenyl)-4,4-dimethyl-2-(1,2,4-triazol-1-yl)-pentan-3-one (see DE-OS (German Published Specification) No. 2,734,426). However, the action of these azole derivatives is not always completely satisfactory especially when small amounts and low concentrations are used.

It has also been disclosed that certain 2-halogenoethyl-triazolylammonium halides have plant growth regulating properties (see U.S. Pat. No. 3,156,554). Thus, for example, an influencing of plant growth, in particular an inhibition of vegetative plant growth, can be achieved in important crop plants with the aid of 2-chloroethyl-trimethyl-ammonium chloride. However, the activity of this substance is not always adequate, especially when small amounts are used.

It has also been disclosed that 2-chloroethyl-phosphonic acid has a growth regulating action (see DE-AS (German Published Specification) No. 1,667,968). However, the results achieved with this substance are likewise not always satisfactory.

The present invention now provides, as new compounds, the 1-allyltriazole derivatives of the general formula

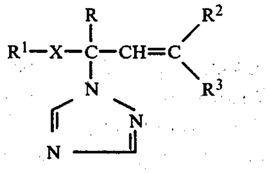

(I)

in which

R represents hydrogen, alkyl or optionally substituted aralkyl, $R^1$ represents optionally substituted alkyl, cycloalkyl or optionally substituted aryl, $R^2$ represents alkyl and $R^3$ represents alkyl, cycloalkyl, optionally substituted cycloalkenyl, alkenyl or optionally substituted aryl, or $R^2$ and $R^3$, together with the carbon atom to which they are bonded, represent optionally substituted cycloalkenyl or cycloalkyl, X represents the group

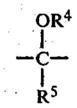

or the keto group, $R^4$ represents hydrogen, alkyl, optionally substituted aralkyl, acyl or optionally substituted carbamoyl and $R^5$ represents hydrogen, alkyl or optionally substituted aralkyl, and acid addition salts and metal salt complexes thereof, especially the salts and complexes that are tolerated by plants.

The 1-allyltriazole derivatives of the formula (I) and acid addition salts and metal salt complexes thereof have powerful fungicidal and plant growth regulating properties and can thus be used as plant protection agents.

Preferably, in the formula (I),

R represents hydrogen, straight-chain or branched alkyl with 1 to 4 carbon atoms or aralkyl with 1 to 2 carbon atoms in the alkyl part and 6 to 10 carbon atoms in the aryl part (especially benzyl) [which aralkyl is optionally substituted by halogen and/or by alkyl with 1 to 4 carbon atoms], $R^1$ represents straight-chain or branched alkyl with 1 to 4 carbon atoms [which optionally carries one or two substituents selected independently from, preferably, halogen, alkylcarbonyloxy with 1 to 4 carbon atoms in the alkyl part, alkylsulphonyloxy with 1 to 4 carbon atoms and phenylsulphonyloxy which is itself optionally substituted by halogen or by alkyl with 1 to 4 carbon atoms], cycloalkyl with 5 to 7 carbon atoms or aryl with 6 to 10 carbon atoms (such as phenyl or naphthyl) [which aryl optionally carries one or more substituents selected independently from, preferably, halogen, alkyl with 1 to 4 carbon atoms, phenyl, phenoxy, halogenophenyl and halogenophenoxy], $R^2$ represents straight-chain or branched alkyl with 1 to 4 carbon atoms, and $R^3$ represents straight-chain or branched alkyl with 1 to 4 carbon atoms, cycloalkyl with 5 to 7 carbon atoms, cycloalkenyl with 5 to 7 carbon atoms [which is optionally substituted by alkyl with 1 to 4 carbon atoms], alkenyl with 2 to 4 carbon atoms or aryl with 6 to 10 carbon atoms (such as phenyl or naphthyl) [which is optionally substituted by, preferably, halogen or alkyl with 1 to 4 carbon atoms], or $R^2$ and $R^3$, together with the carbon atom to which they are bonded, represent cycloalkenyl with 5 to 7 carbon atoms [which is optionally substituted by alkyl with 1 to 4 carbon atoms] or cycloalkyl with 3 to 12 carbon atoms which is optionally substituted by alkyl with 1 to 4 carbon atoms, halogen, cyano or alkylene or alkylidene with 2 to 4 carbon atoms, X represents the group $—C(OR^4)R^5—$ or the keto group, $R^4$ represents hydrogen, straight-chain or branched alkyl with 1 to 4 carbon atoms, aralkyl with 1 to 2 carbon atoms in the alkyl part and 6 to 10 carbon atoms in the aryl part (such as benzyl or naphthylmethyl) [which optionally carries one or more substituents selected independently from, preferably, halogen, alkyl with 1 to 4 carbon atoms, halogenoalkyl with up to 2 carbon atoms and up to 3 identical or different halogen atoms (preferred halogen atoms being fluorine and chlorine) and phenyl and phenoxy, the last two being themselves optionally substituted by halogen], the acyl radical $—CO—R^{10}$ or the carbamoyl radical $—CO—NR^{11}R^{12}$, $R^5$ represents hydrogen, alkyl with 1 to 4 carbon atoms or aralkyl with 1 to 2 carbon atoms in the alkyl part and 6 to 10 carbon atoms in the aryl part (such as benzyl) [which is optionally substituted by halogen or alkyl with 1 to 4 carbon atoms], $R^{10}$ represents straight-chain or branched alkyl with 1 to 4 carbon atoms, halogenoalkyl with 1 to 2 carbon atoms and 1 to 5 identical or different halogen atoms (preferably fluorine and chlorine atoms) or phenyl or benzyl [either of which is optionally substituted by, preferably, halogen or alkyl with 1 to 4 carbon atoms], $R^{11}$ represents hydrogen or alkyl with 1 to 4 carbon atoms, and $R^{12}$ represents alkyl with 1 to 8 carbon atoms, halogenoalkyl with up to 4 carbon atoms and up to 5 identical or different halogen atoms (especially fluorine or chlorine atoms), aryl with 6 to 10 carbon atoms (such as phenyl or naphthyl) [which optionally carries one or more substituents selected independently from, preferably, halogen, alkyl with 1 to 4 carbon atoms and halogenoalkyl with up to 2 carbon atoms and up to 5 identical or different halogen atoms (especially fluorine and chlorine atoms)] or halogenoalkylmercapto with 1 to 2 carbon atoms and up to 5 halogen atoms (especially fluorine and chlorine atoms).

If appropriate, the compounds of the formula (I) can exist in two geometric isomer forms; depending on the arrangement of the groups which are bonded to the double bond. If X represents the group $—C(OR^4)R^5—$, two asymmetric carbon atoms are present, so that the compounds of the formula (I) exist in two diastereomeric forms and as four optical isomers. The formula (I) therefore embraces both dual isomers and mixtures of the various isomers.

The invention also provides a process for the preparation of a 1-allyl-triazole derivative of the formula (I) or an acid addition salt or metal salt complex thereof, in which (a) a triazole-ketone of the general formula

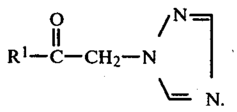

(II)

in which $R^1$ has the meaning indicated above, is reacted with an aldehyde of the general formula

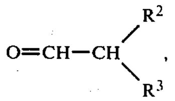

(III)

in which $R^2$ and $R^3$ have the meanings indicated above, in the presence of a solvent and in the presence of a catalyst, and the desired product of the general formula

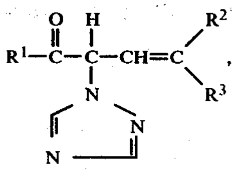

(Ia)

in which $R^1$, $R^2$ and $R^3$ have the meanings indicated above, is isolated, or (b) a compound of the general formula (Ia), obtainable by process (a) is, in a manner which is in itself known, (α) reduced with a complex hydride in the presence of a solvent or (β) reduced with a Grignard compound of the general formula $$R^6—Mg—Hal \quad (IV),$$

in which $R^6$ represents alkyl or optionally substituted aralkyl and

Hal represents halogen, in the presence of a solvent, or a compound, obtainable by process variant (b), of the general formula

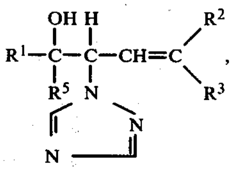

(Ib)

in which $R^1$, $R^2$, $R^3$ and $R^5$ have the meanings indicated above, (c) is reated with a halide of the general formula $$R^7—Hal \quad (V),$$

in which $R^7$ represents alkyl, optionally substituted aralkyl, acyl or optionally substituted carbamoyl and Hal represents halogen, in the presence of a solvent and if appropriate in the presence of a strong base or if appropriate in the presence of an acid-binding agent, or (d) is reacted with acid anhydrides of the general formula $$R^8—O—R^8 \quad (VI),$$

in which $R^8$ represents acyl, in the presence of a solvent and if appropriate in the presence of a catalyst, or (e) is reacted with an isocyanate of the general formula $$O=C=N—R^9 \quad (VII),$$

in which $R^9$ represents alkyl, halogenoalkyl or optionally substituted aryl, in the presence of a solvent and if appropriate in the presence of a catalyst, or (f) a compound of the general formula (Ia), obtainable by process variant (a), is reacted with a halide of the general formula Y—Hal (VIII), in which Y represents alkyl or optionally substituted aralkyl and Hal represents halogen, in the presence of a strong base and in the presence of a solvent, and the resulting compound of the general formula

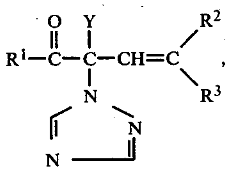
(Iaa)

in which $R^1$, $R^2$, $R^3$ and Y have the manings indicated above, is optionally reacted further, analogously to process variant (b), (c), (d) or (e), and, if required, an acid or a metal salt is then added onto the product of any of process variants (a) to (f).

Surprisingly, the 1-allyltriazole derivatives according to the invention, including the salts and complexes, exhibit a better fungicidal action than the acylated and carbamoylated derivatives of 3,3-dimethyl-1-triazolyl-butan-2-ols substituted in the phenyl part, which are known from the state of the art, and 1-(4-chlorophenyl)-4,4-dimethyl-2-(1,2,4-triazol-1-yl)-pentan-3-one, which is likewise known, which are closely related compounds chemically and from the point of view of their action.

Furthermore, the allyltriazole derivatives according to the invention, including the acid addition salts and metal salt complexes, exhibit a better plant growth regulating action than 2-chloroethyl-trimethylammonium chloride, which is known, and than 2-chloroethylphosphonic acid, which is likewise known, which are recognized as substances of good activity and the same type of action. The substances according to the invention thus represent a valuable enrichment of the art.

Very particularly preferred compounds of the formula (I) are those in which R represents hydrogen, methyl, ethyl, benzyl, chlorobenzyl or dichlorobenzyl; $R^1$ represents tert.-butyl, isopropyl, chloro-tert.-butyl, bromo-tert.-butyl, fluoro-tert.-butyl, acetoxy-tert.-butyl, methylsulphonyloxy-tert.-butyl, p-toluenesulphonyloxy-tert.-butyl, 1,3-dichloro-2-methyl-prop-2-yl, 1,3-dibromo-2-methyl-prop-2-yl, 1,3-difluoro-2-methyl-prop-2-yl, 1-chloro-3-bromo-2-methyl-prop-2-yl, 1,3-diacetoxy-2-methyl-prop-2-yl, cyclohexyl, phenyl, chlorophenyl bromophenyl, dichlorophenyl, fluorophenyl, methylphenyl, dimethylphenyl, chloro-methylphenyl, biphenylyl, phenoxyphenyl, chlorophenylphenyl or chlorophenoxyphenyl; $R^2$ represents methyl, ethyl, propyl or butyl and $R^3$ represents methyl, ethyl, isopropyl, cyclohexyl, cyclohexenyl, methylcyclohexenyl, allyl, methacryl, phenyl, chlorophenyl, dichlorophenyl or methylphenyl; or $R^2$ and $R^3$, together with the carbon atom to which they are bonded, represent cyclopropyl, cyclobutyl, cyclopentyl; cyclohexyl, which is optionally substituted by chlorine, bromine, methyl, or cyano; norbornyl, which is optionally substituted by methyl or cyano; cyclododecanyl; cyclohexenyl, methylcylohexenyl; norbornenyl, tricyclodecanyl or tricycloundecanyl; X represents the group —C(OR⁴)R⁵— or the keto groupl $R^4$ represents hydrogen, methyl, ethyl, n-propyl, isopropyl, isobutyl, naphthyl which is optionally substituted by chlorine, benzyl which is optionally monosubstituted or polysubstituted by identical or different substituents from the group consisting of chlorine, fluorine, methyl, phenyl, chlorophenyl, phenoxy and chlorophenoxy, the acyl radical —CO—$R^{10}$ or the carbamoyl radical —CO—$NR^{11}R^{12}$; $R^5$ represents hydrogen, methyl, ethyl, isopropyl, benzyl, chlorobenzyl or dichlorobenzyl; $R^{10}$ represents methyl, ethyl, isopropyl, isobutyl, chloromethyl, dichloromethyl or phenyl or benzyl, either of which is optionally monosubstituted or polysubstituted, the substituents being chlorine, bromine or methyl; $R^{11}$ represents hydrogen, methyl or ethyl; and $R^{12}$ represents methyl, ethyl, chloroethyl, phenyl, chlorophenyl, trifluoromethyl-, chlorodifluoro-methyl-, dichlorofluoro-methyl- or trichloro-methyl-mercapto.

The following compounds of the general formula (I) may be mentioned specifically, in addition to the compounds mentioned later in the preparative examples (where a sngle radical is listed for $R^2$ and $R^3$ together it includes the carbon atom to which they are attached and, when a name rather than a structural formula is given, the name is that of the compound rather than the divalent-ylidene radical):

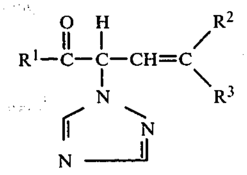
(Ia)

| $R^1$ | $R^2$ | $R^3$ |
|---|---|---|
| $C(CH_3)_3$ | $C_2H_5$ | $C_2H_5$ |
| $C(CH_3)_3$ | $C_2H_5$ | $CH_3$ |
| $C(CH_3)_3$ | $CH_3$ | $CH_3$ |

-continued
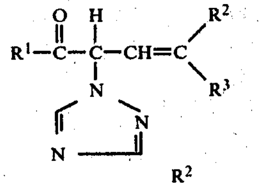
(Ia)
| R¹ | R² | R³ |
|---|---|---|
| C(CH₃)₃ | CH₃ | 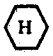 |
| C(CH₃)₃ | CH₃ | 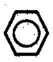 |
| C(CH₃)₃ | | Cyclopropane |
| C(CH₃)₃ | | Cyclobutane |
| C(CH₃)₃ | | Cyclopentane |
| C(CH₃)₃ | | Cycloheptane |
| C(CH₃)₃ | | Norborn-3-ene-2 |
| 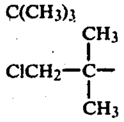 | | Cyclohexane |
| 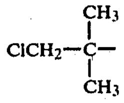 | | Cyclohexene |
| 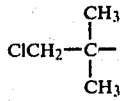 | | Methylcyclohexene |
| 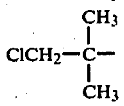 | CH₃ | CH₃ |
| 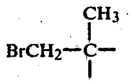 | | Cyclohexane |
| 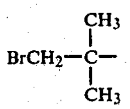 | | Cyclohexene |
| 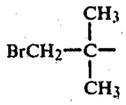 | | Methylcyclohexene |
| 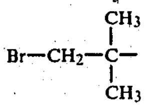 | | Methylcyclohexene |
| 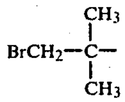 | CH₃ | CH₃ |
| 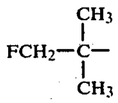 | | Cyclohexane |
| 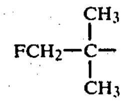 | | Cyclohexene |
| 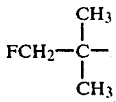 | | Methylcyclohexene |
| 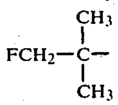 | CH₃ | CH₃ |

-continued
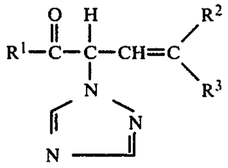
(Ia)
| $R^1$ | $R^2$ | $R^3$ |
|---|---|---|
| 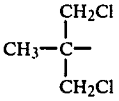 | | Cyclohexane |
| 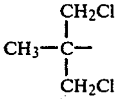 | | Cyclohexene |
| 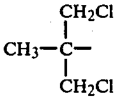 | | Methylcyclohexene |
| 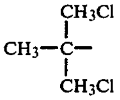 | $CH_3$ | $CH_3$ |
| 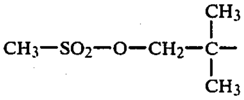 | | Cyclohexane |
| 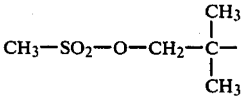 | | Cyclohexene |
| 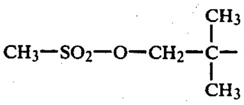 | | Methylcyclohexene |
| 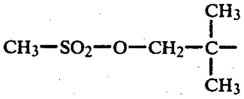 | $CH_3$ | $CH_3$ |
| 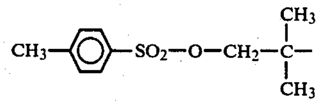 | | Cyclohexane |
| 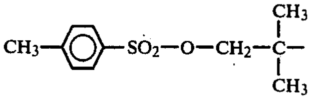 | | Cyclohexene |
| 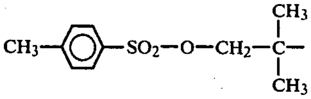 | | Methylcyclohexene |
| 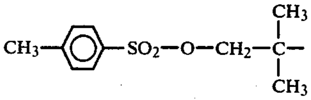 | $CH_3$ | $CH_3$ |
| 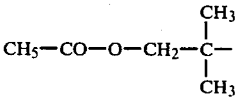 | | Cyclohexane |
| 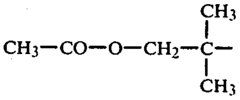 | | Cyclohexene |
| 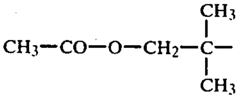 | | Methylcyclohexene |

-continued
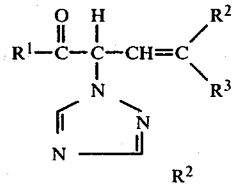 (Ia)
| $R^1$ | $R^2$ | $R^3$ |
|---|---|---|
| 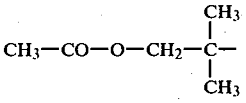 | $CH_3$ | $CH_3$ |
| 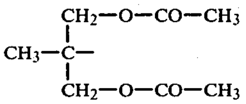 | Cyclohexane | |
| 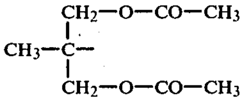 | Cyclohexene | |
| 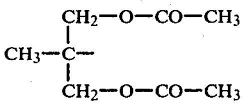 | Methylcyclohexene | |
| 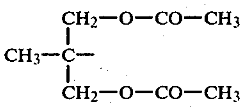 | $CH_3$ | $CH_3$ |
| 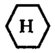 | Cyclohexane | |
| 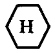 | Cyclohexene | |
| 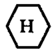 | Methylcyclohexene | |
| 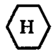 | $CH_3$ | $CH_3$ |
| 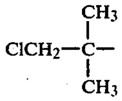 | $CH_3$ $CH_3$ | $C_2H_5$ |
| 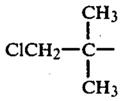 | Cyclohexane | $C_2H_5$ |
| 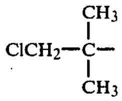 | Cyclohexene | $C_2H_5$ |
| 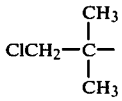 | $CH_3$ $CH_3$ | 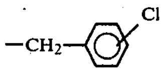 |
| 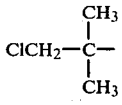 | Cyclohexane | 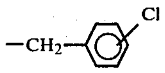 |
| 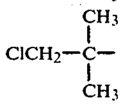 | Cyclohexene | 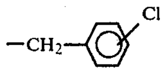 |
| 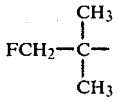 | $CH_3$ $CH_3$ | $C_2H_5$ |

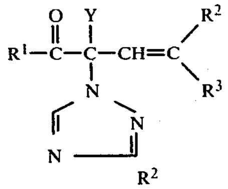
(Iaa)

| R¹ | R² | R³ | Y |
|---|---|---|---|
| $C(CH_3)_3$ | $C_2H_5$ | $CH_3$ | $CH_3$ |
| $C(CH_3)_3$ | $C_2H_5$ | $C_2H_5$ | $CH_3$ |
| $C(CH_3)_3$ | Cyclohexane | | $CH_3$ |
| $C(CH_3)_3$ | Cyclohexene | | $CH_3$ |
| $C(CH_3)_3$ | $C_2H_5$ | $CH_3$ | $C_2H_5$ |
| $C(CH_3)_3$ | $C_2H_5$ | $C_2H_5$ | $C_2H_5$ |
| $C(CH_3)_3$ | Cyclohexane | | $C_2H_5$ |
| $C(CH_3)_3$ | Cyclohexene | | $C_2H_5$ |
| $C(CH_3)_3$ | $C_2H_5$ | $CH_3$ | 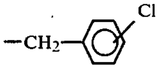 |
| $C(CH_3)_3$ | $C_2H_5$ | $C_2H_5$ | 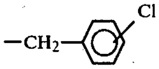 |
| $C(CH_3)_3$ | Cyclohexane | | 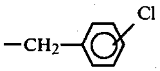 |
| $C(CH_3)_3$ | Cyclohexene | | 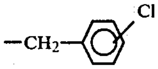 |
| 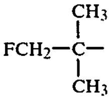 | Cyclohexane | | $C_2H_5$ |
| 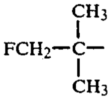 | Cyclohexene | | $C_2H_5$ |
| 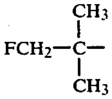 | $CH_3$ | $CH_3$ | 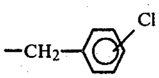 |
| 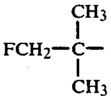 | Cyclohexane | | 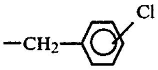 |
| 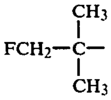 | Cyclohexene | | 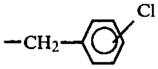 |
| 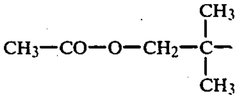 | $CH_3$ | $CH_3$ | $C_2H_5$ |
| 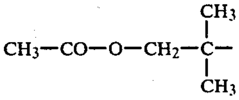 | Cyclohexane | | $C_2H_5$ |
| 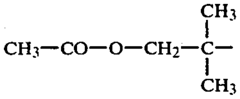 | Cyclohexene | | $C_2H_5$ |
| 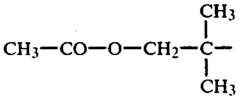 | $CH_3$ | $CH_3$ | 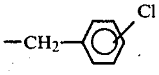 |
| 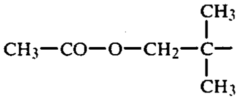 | Cyclohexane | | 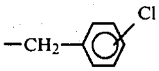 |
| 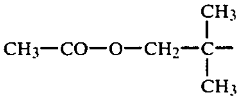 | Cyclohexene | | 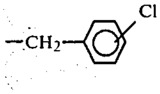 |

-continued

| | | | |
|---|---|---|---|
| 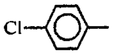 | $CH_3$ | $CH_3$ | $C_2H_5$ |
| 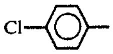 | Cyclohexane | | $C_2H_5$ |
| 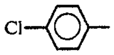 | Cyclohexene | | $C_2H_5$ |
| 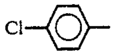 | $CH_3$ | $CH_3$ | 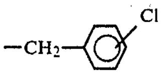 |
| 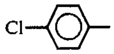 | Cyclohexane | | 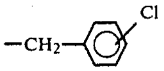 |
| 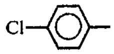 | Cyclohexene | | 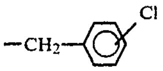 |
| 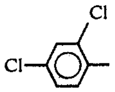 | $CH_3$ | $CH_3$ | $C_2H_5$ |
| 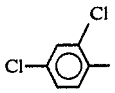 | Cyclohexane | | $C_2H_5$ |
| 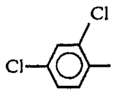 | Cyclohexene | | $C_2H_5$ |
| 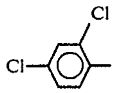 | $CH_3$ | $CH_3$ | 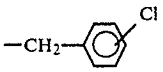 |
| 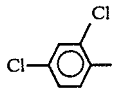 | Cyclohexane | | 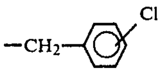 |
| 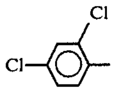 | Cyclohexene | | 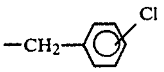 |

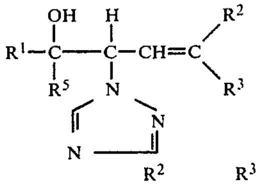

(Ib)

| $R^1$ | $R^2$ | $R^3$ | $R^5$ |
|---|---|---|---|
| $C(CH_3)_3$ | $C_2H_5$ | $CH_3$ | H |
| $C(CH_3)_3$ | $CH_3$ | $CH_3$ | H |
| $C(CH_3)_3$ | $CH_3$ | 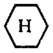 | H |
| $C(CH_3)_3$ | $CH_3$ | 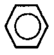 | H |
| $C(CH_3)_3$ | Cyclopropane | | H |
| $C(CH_3)_3$ | Cyclobutane | | H |
| $C(CH_3)_3$ | Cyclopentane | | H |
| $C(CH_3)_3$ | Cycloheptane | | H |
| $C(CH_3)_3$ | $CH_3$ | $CH_3$ | $CH_3$ |
| $C(CH_3)_3$ | Cyclohexane | | $CH_3$ |
| $C(CH_3)_3$ | Cyclohexene | | $CH_3$ |
| $C(CH_3)_3$ | Methylcyclohexene | | $CH_3$ |
| $C(CH_3)_3$ | $CH_3$ | $CH_3$ | 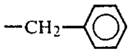 |
| $C(CH_3)_3$ | Cyclohexane | | 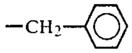 |
| $C(CH_3)_3$ | Cyclohexene | | 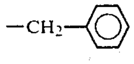 |
| $C(CH_3)_3$ | Methylcyclohexene | | 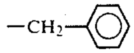 |

-continued
| | | | |
|---|---|---|---|
| 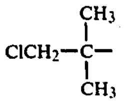 | CH₃ | CH₃ | H |
| 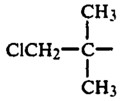 | Cyclohexane | | H |
| 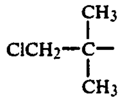 | Cyclohexene | | H |
| 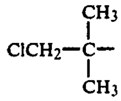 | Methylcyclohexene | | H |
| 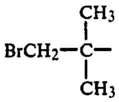 | $CH_3$ | $CH_3$ | H |
| 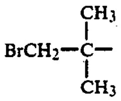 | Cyclohexane | | H |
| 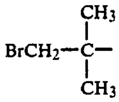 | Cyclohexene | | H |
| 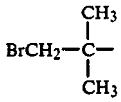 | Methylcyclohexene | | H |
| 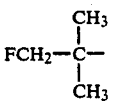 | $CH_3$ | $CH_3$ | H |
| 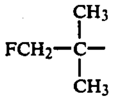 | Cyclohexane | | H |
| 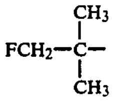 | Cyclohexene | | H |
| 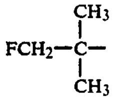 | Methylcyclohexene | | H |
| 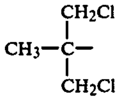 | $CH_3$ | $CH_3$ | H |
| 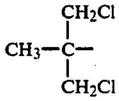 | Cyclohexane | | H |
| 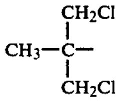 | Cyclohexene | | H |
| 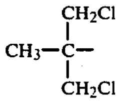 | Methylcyclohexene | | H |
| 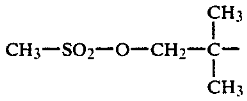 | $CH_3$ | $CH_3$ | H |

-continued
| | | | |
|---|---|---|---|
| 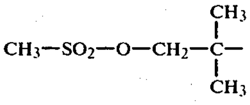 | Cyclohexane | | H |
| 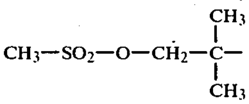 | Cyclohexene | | H |
| 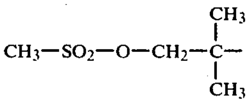 | Methylcyclohexene | | H |
| 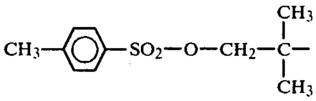 | $CH_3$ | $CH_3$ | H |
| 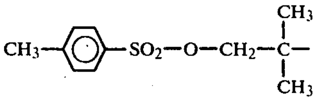 | Cyclohexane | | H |
| 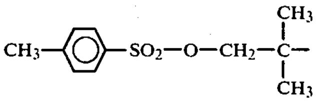 | Cyclohexene | | H |
| 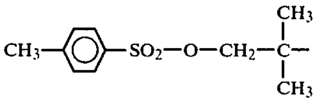 | Methylcyclohexene | | H |
| 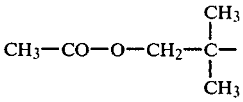 | $CH_3$ | $CH_3$ | H |
| 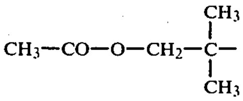 | Cyclohexane | | H |
| 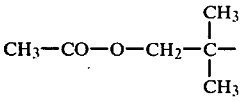 | Cyclohexene | | H |
| 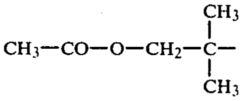 | Methylcyclohexene | | H |
| 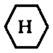 | $CH_3$ | $CH_3$ | H |
| 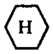 | Cyclohexane | | H |
| 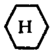 | Cyclohexene | | H |
| 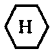 | Methylcyclohexene | | H |
| 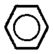 | $CH_3$ | $CH_3$ | H |
| 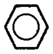 | Cyclohexane | | H |
| 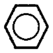 | Cyclohexene | | H |
| 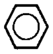 | Methylcyclohexene | | H |
| 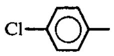 | Cyclohexane | | H |
| 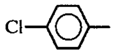 | Cyclohexene | | H |

-continued

| | | | |
|---|---|---|---|
| 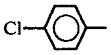 | Methylcyclohexene | | H |
| 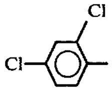 | $CH_3$ | $CH_3$ | H |
| 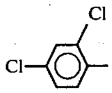 | Cyclohexane | | H |
| 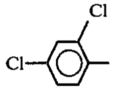 | Cyclohexene | | H |
| 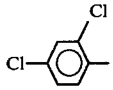 | Methylcyclohexene | | H |

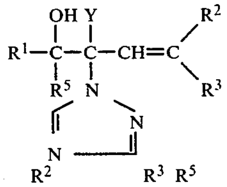

(Ibb)

| $R^1$ | $R^2$ | $R^3$ | $R^5$ | Y |
|---|---|---|---|---|
| $C(CH_3)_3$ | $CH_3$ | $CH_3$ | H | $C_2H_5$ |
| $C(CH_3)_3$ | $C_2H_5$ | $CH_3$ | H | $C_2H_5$ |
| $C(CH_3)_3$ | $C_2H_5$ | $C_2H_5$ | H | $C_2H_5$ |
| $C(CH_3)_3$ | Cyclohexane | | H | $C_2H_5$ |
| $C(CH_3)_3$ | Cyclohexene | | H | $C_2H_5$ |
| $C(CH_3)_3$ | $CH_3$ | $CH_3$ | $CH_3$ | $C_2H_5$ |
| $C(CH_3)_3$ | $C_2H_5$ | $CH_3$ | $CH_3$ | $C_2H_5$ |
| $C(CH_3)_3$ | $C_2H_5$ | $C_2H_5$ | $CH_3$ | $C_2H_5$ |
| $C(CH_3)_3$ | Cyclohexane | | $CH_3$ | $C_2H_5$ |
| $C(CH_3)_3$ | Cyclohexene | | $CH_3$ | $C_2H_5$ |
| $C(CH_3)_3$ | $CH_3$ | $CH_3$ | H | 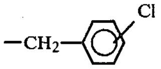 |
| $C(CH_3)_3$ | $C_2H_5$ | $CH_3$ | H | 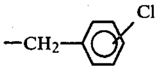 |
| $C(CH_3)_3$ | $C_2H_5$ | $C_2H_5$ | H | 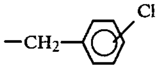 |
| $C(CH_3)_3$ | Cyclohexane | | H | 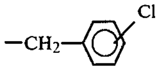 |
| $C(CH_3)_3$ | Cyclohexene | | H | 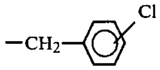 |
| $C(CH_3)_3$ | $CH_3$ | $CH_3$ | $CH_3$ | 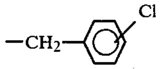 |
| $C(CH_3)_3$ | $C_2H_5$ | $CH_3$ | $CH_3$ | 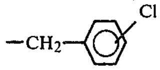 |
| $C(CH_3)_3$ | $C_2H_5$ | $C_2H_5$ | $CH_3$ | 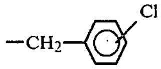 |
| $C(CH_3)_3$ | Cyclohexane | | $CH_3$ | 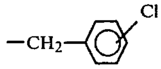 |
| $C(CH_3)_3$ | Cyclohexene | | $CH_3$ | 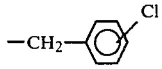 |
| 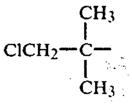 | $CH_3$ | $CH_3$ | H | 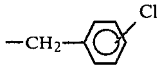 |

-continued (Ibb)

| $R^1$ | $R^2$ | $R^3$ | $R^5$ | Y |
|---|---|---|---|---|
| 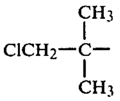 | Cyclohexane | | H | 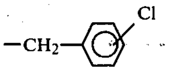 |
| 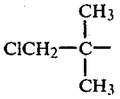 | Cyclohexene | | H | 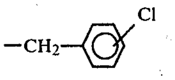 |
| 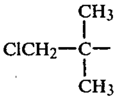 | $CH_3$ | $CH_3$ | $CH_3$ | 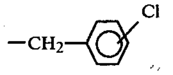 |
| | Cyclohexane | | $CH_3$ | 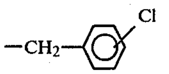 |
| | Cyclohexene | | $CH_3$ | 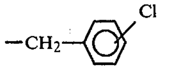 |
| 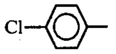 | $CH_3$ | $CH_3$ | H | 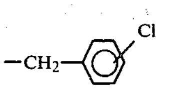 |
| 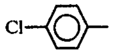 | Cyclohexane | | H | 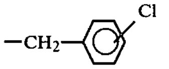 |
| 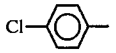 | Cyclohexene | | H | 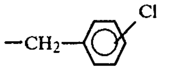 |
| 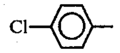 | $CH_3$ | $CH_3$ | $CH_3$ | 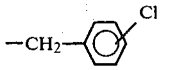 |
| 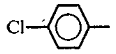 | Cyclohexane | | $CH_3$ | 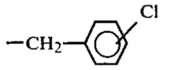 |
| 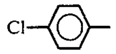 | Cyclohexene | | $CH_3$ | 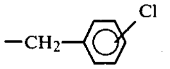 |
| 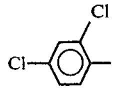 | $CH_3$ | $CH_3$ | H | 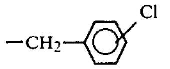 |

-continued

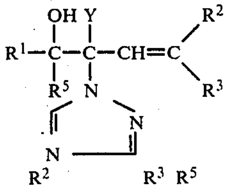 (Ibb)

| $R^1$ | $R^2$ | $R^3$ | $R^5$ | Y |
|---|---|---|---|---|
| 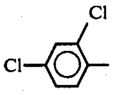 | Cyclohexane | | H | 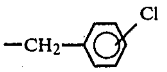 |
| 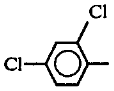 | Cyclohexene | | H | 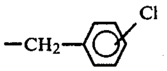 |
| 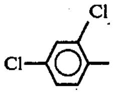 | $CH_3$ | $CH_3$ | $CH_3$ | 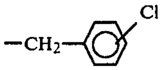 |
| 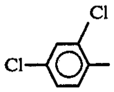 | Cyclohexane | | $CH_3$ | 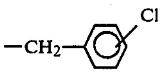 |
| 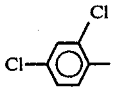 | Cyclohexene | | $CH_3$ | 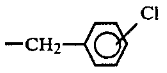 |

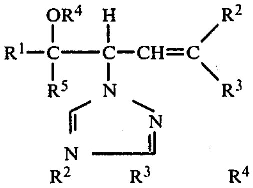 (Ic)

| $R^1$ | $R^2$ | $R^3$ | $R^4$ | $R^5$ |
|---|---|---|---|---|
| $C(CH_3)_3$ | $CH_3$ | $CH_3$ | $C_2H_5$ | H |
| $C(CH_3)_3$ | Cyclohexane | | $C_2H_5$ | H |
| $C(CH_3)_3$ | Cyclohexene | | $C_2H_5$ | H |
| $C(CH_3)_3$ | Methylcyclohexene | | $C_2H_5$ | H |
| $CH_3$<br>$ClCH_2-C-$<br>$CH_3$ | $CH_3$ | $CH_3$ | $C_2H_5$ | $CH_3$ |
| $CH_3$<br>$ClCH_2-C-$<br>$CH_3$ | Cyclohexane | | $C_2H_5$ | $CH_3$ |
| $CH_3$<br>$ClCH_2-C-$<br>$CH_3$ | Cyclohexene | | $C_2H_5$ | $CH_3$ |
| $CH_3$<br>$ClCH_2-C-$<br>$CH_3$ | Methylcyclohexene | | $C_2H_5$ | $CH_3$ |
| $CH_3$<br>$FCH_2-C-$<br>$CH_3$ | $CH_3$ | $CH_3$ | $C_2H_5$ | H |
| $CH_3$<br>$FCH_2-C-$<br>$CH_3$ | Cyclohexane | | $C_2H_5$ | H |
| $CH_3$<br>$FCH_2-C-$<br>$CH_3$ | Cyclohexene | | $C_2H_5$ | H |

-continued

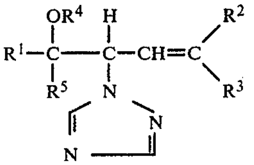 (Ic)

| $R^1$ | $R^2$ | $R^3$ | $R^4$ | $R^5$ |
|---|---|---|---|---|
| $CH_3$<br>$FCH_2-C-$<br>$CH_3$ | Methylcyclohexene | | $C_2H_5$ | H |
| 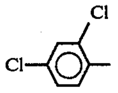 | $CH_3$ | $CH_3$ | $C_2H_5$ | H |
| 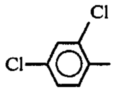 | Cyclohexane | | $C_2H_5$ | H |
| 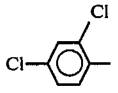 | Cyclohexene | | $C_2H_5$ | H |
| 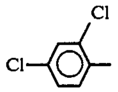 | Methylcyclohexene | | $C_2H_5$ | H |
| $C(CH_3)_3$ | $CH_3$ | $CH_3$ | 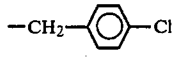 | H |
| $C(CH_3)_3$ | Cyclohexane | | 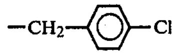 | H |
| $C(CH_3)_3$ | Cyclohexene | | 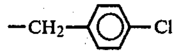 | H |
| $C(CH_3)_3$ | Methylcyclohexene | | 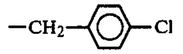 | H |
| $CH_3$<br>$ClCH_2-C-$<br>$CH_3$ | $CH_3$ | $CH_3$ | 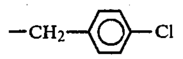 | H |
| $CH_3$<br>$ClCH_2-C-$<br>$CH_3$ | Cyclohexane | | 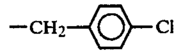 | H |
| $CH_3$<br>$ClCH_2-C-$<br>$CH_3$ | Cyclohexene | | 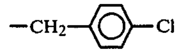 | H |
| $CH_3$<br>$ClCH_2-C-$<br>$CH_3$ | Methylcyclohexene | | 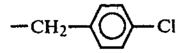 | H |
| $CH_3$<br>$FCH_2-C-$<br>$CH_3$ | $CH_3$ | $CH_3$ | 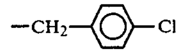 | H |
| $CH_3$<br>$FCH_2-C-$<br>$CH_3$ | Cyclohexane | | 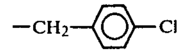 | H |
| $CH_3$<br>$FCH_2-C-$<br>$CH_3$ | Cyclohexene | | 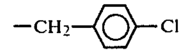 | H |
| $CH_3$<br>$FCH_2-C-$<br>$CH_3$ | Methylcyclohexene | | 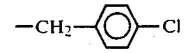 | H |

-continued

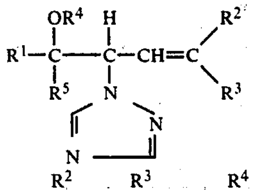 (Ic)

| $R^1$ | $R^2$ | $R^3$ | $R^4$ | $R^5$ |
|---|---|---|---|---|
| 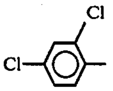 | $CH_3$ | $CH_3$ | 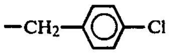 | H |
| 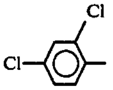 | Cyclohexane | | 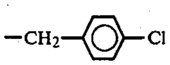 | H |
| 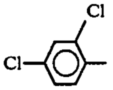 | Cyclohexene | | 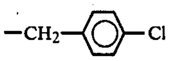 | H |
| 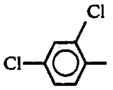 | Methylcyclohexene | | 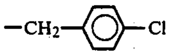 | H |
| 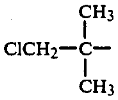 | $CH_3$ | $CH_3$ | $-CO-CH_3$ | H |
| 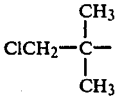 | Cyclohexane | | $-CO-CH_3$ | H |
| 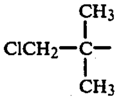 | Cyclohexene | | $-CO-CH_3$ | H |
| 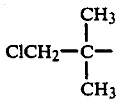 | Methylcyclohexene | | $-CO-CH_3$ | H |
| 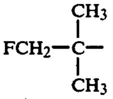 | $CH_3$ | $CH_3$ | $-CO-CH_3$ | H |
| 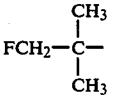 | Cyclohexane | | $-CO-CH_3$ | H |
| 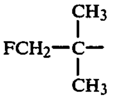 | Cyclohexene | | $-CO-CH_3$ | H |
| 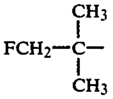 | Methylcyclohexene | | $-CO-CH_3$ | H |
| 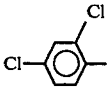 | $CH_3$ | $CH_3$ | $-CO-CH_3$ | H |
| 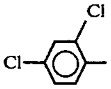 | Cyclohexane | | $-CO-CH_3$ | H |
| 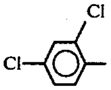 | Cyclohexene | | $-CO-CH_3$ | H |
| 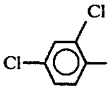 | Methylcyclohexene | | $-CO-CH_3$ | H |

-continued

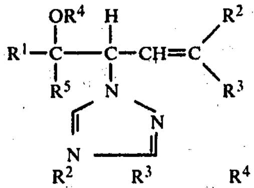 (Ic)

| $R^1$ | $R^2$ | $R^3$ | $R^4$ | $R^5$ |
|---|---|---|---|---|
| 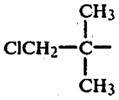 | $CH_3$ | $CH_3$ | $-CO-NHCH_3$ | H |
| 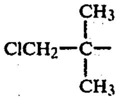 | Cyclohexane | | $-CO-NHCH_3$ | H |
| 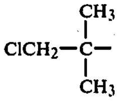 | Cyclohexene | | $-CO-NHCH_3$ | H |
| 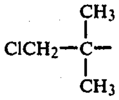 | Methylcyclohexene | | $-CO-NHCH_3$ | H |
| 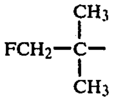 | $CH_3$ | $CH_3$ | $-CO-NHCH_3$ | H |
| 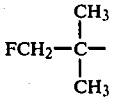 | Cyclohexane | | $-CO-NHCH_3$ | H |
| 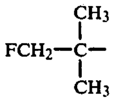 | Cyclohexene | | $-CO-NHCH_3$ | H |
| 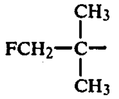 | Methylcyclohexene | | $-CO-NHCH_3$ | H |
| 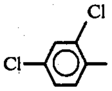 | $CH_3$ | $CH_3$ | $-CO-NHCH_3$ | H |
| 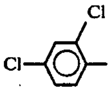 | Cyclohexane | | $-CO-NHCH_3$ | H |
| 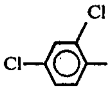 | Cyclohexene | | $-CO-NHCH_3$ | H |
| 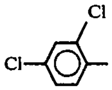 | Methylcyclohexene | | $-CO-NHCH_3$ | H |
| 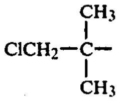 | $CH_3$ | $CH_3$ | 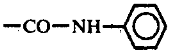 | H |
| 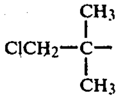 | Cyclohexane | | 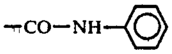 | H |
| 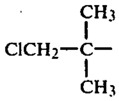 | Cyclohexene | | | H |
| 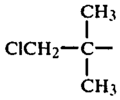 | Methylcyclohexene | | | H |

-continued

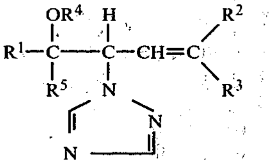

(Ic)

| $R^1$ | $R^2$ | $R^3$ | $R^4$ | $R^5$ |
|---|---|---|---|---|
| | $CH_3$ | $CH_3$ | —CO—NH—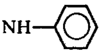 | H |
| | Cyclohexane | | —CO—NH—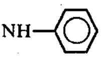 | H |
| | Cyclohexene | | —CO—NH—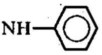 | H |
| | Methylcyclohexene | | —CO—NH—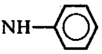 | H |
| 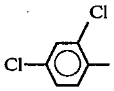 | $CH_3$ | $CH_3$ | —CO—NH—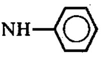 | H |
| 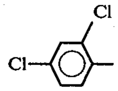 | Cyclohexane | | —CO—NH—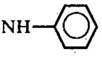 | H |
| 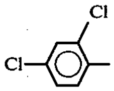 | Cyclohexene | | —CO—NH—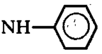 | H |
| 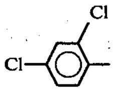 | Methylcyclohexene | | —CO—NH—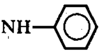 | H |
| | $CH_3$ | $CH_3$ | —CO—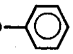 | H |
| | Cyclohexane | | —CO—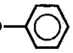 | H |
| | Cyclohexene | | —CO—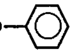 | H |
| | Methylcyclohexene | | —CO—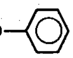 | H |
| | $CH_3$ | $CH_3$ | —CO—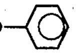 | H |
| | Cyclohexane | | —CO—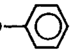 | H |
| | Cyclohexene | | —CO—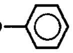 | H |
| | Methylcyclohexene | | —CO—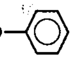 | H |

-continued

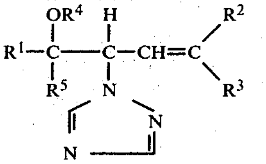

(Ic)

| $R^1$ | $R^2$ | $R^3$ | $R^4$ | $R^5$ |
|---|---|---|---|---|
| 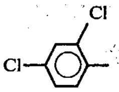 | $CH_3$ | $CH_3$ | —CO—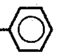 | H |
| 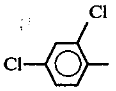 | Cyclohexane | | —CO—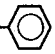 | H |
| 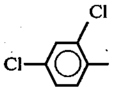 | Cyclohexene | | —CO—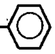 | H |
| 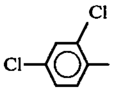 | Methylcyclohexene | | —CO—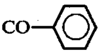 | H |
| | $CH_3$ | $CH_3$ | $—CO—CHCl_2$ | H |
| | Cyclohexane | | $—CO—CHCl_2$ | H |
| | Cyclohexene | | $—CO—CHCl_2$ | H |
| | Methylcyclohexene | | $—CO—CHCl_2$ | H |
| | $CH_3$ | $CH_3$ | $—CO—CHCl_2$ | H |
| | Cyclohexane | | $—CO—CHCl_2$ | H |
| | Cyclohexene | | $—CO—CHCl_2$ | H |
| | Methylcyclohexene | | $—CO—CHCl_2$ | H |
| 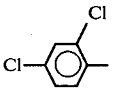 | $CH_3$ | $CH_3$ | $—CO—CHCl_2$ | H |
| 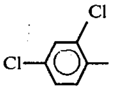 | Cyclohexane | | $—CO—CHCl_2$ | H |
| 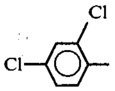 | Cyclohexene | | $—CO—CHCl_2$ | H |
| 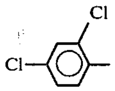 | Methylcyclohexene | | $—CO—CHCl_2$ | H |
| $C(CH_3)_3$ | $CH_3$ | $CH_3$ | $—CO—CH_3$ | H |

-continued

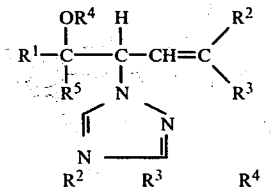

(Ic)

| $R^1$ | $R^2$ | $R^3$ | $R^4$ | $R^5$ |
|---|---|---|---|---|
| $C(CH_3)_3$ | Cyclohexane | | $-CO-CH_3$ | H |
| $C(CH_3)_3$ | Cyclohexene | | $-CO-CH_3$ | H |
| $C(CH_3)_3$ | Methylcyclohexene | | $-CO-CH_3$ | H |
| $C(CH_3)_3$ | $CH_3$ | $CH_3$ | $-CO-NHCH_3$ | H |
| $C(CH_3)_3$ | Cyclohexane | | $-CO-NHCH_3$ | H |
| $C(CH_3)_3$ | Cyclohexene | | $-CO-NHCH_3$ | H |
| $C(CH_3)_3$ | Methylcyclohexene | | $-CO-NHCH_3$ | H |
| $C(CH_3)_3$ | $CH_3$ | $CH_3$ | —CO—NH— 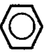 | H |
| $C(CH_3)_3$ | Cyclohexane | | —CO—NH— 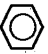 | H |
| $C(CH_3)_3$ | Cyclohexene | | —CO—NH— 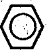 | H |
| $C(CH_3)_3$ | Methylcyclohexene | | —CO—NH— 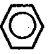 | H |
| $C(CH_3)_3$ | $CH_3$ | $CH_3$ | —CO— 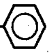 | H |
| $C(CH_3)_3$ | Cyclohexane | | —CO— 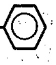 | H |
| $C(CH_3)_3$ | Cyclohexene | | —CO— 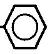 | H |
| $C(CH_3)_3$ | Methylcyclohexene | | —CO— 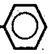 | H |
| $C(CH_3)_3$ | $CH_3$ | $CH_3$ | $-CO-CHCl_2$ | H |
| $C(CH_3)_3$ | Cyclohexane | | $-CO-CHCl_2$ | H |
| $C(CH_3)_3$ | Cyclohexene | | $-CO-CHCl_2$ | H |
| $C(CH_3)_3$ | Methylcyclohexene | | $-CO-CHCl_2$ | H |

If, for example, pinacolyl-1,2,4-triazole and cyclohexanecarbaldehyde are used as starting materials in process variant (a), the course of the reaction can be represented by the following equation:

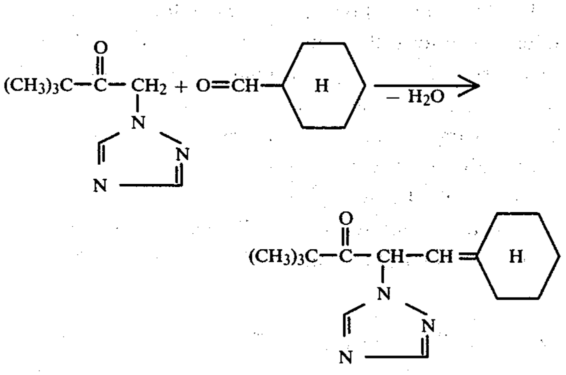

If 1-cyclohexylidene-4,4-dimethyl-2-(1,2,4-triazol-1-yl)-pentan-3-one and sodium borohydride are used as starting materials in process variant (b)(β), the course of the reaction can be represented by the following equation:

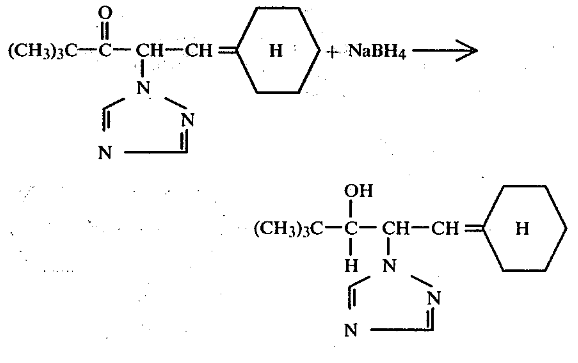

If 1-cyclohexylidene-4,4-dimethyl-2-(1,2,4-triazol-1-yl)-pentan-3-one and methyl-magnesium bromide are used as starting materials in process variant (b)(β), the course of the reaction can be representated by the following equation:

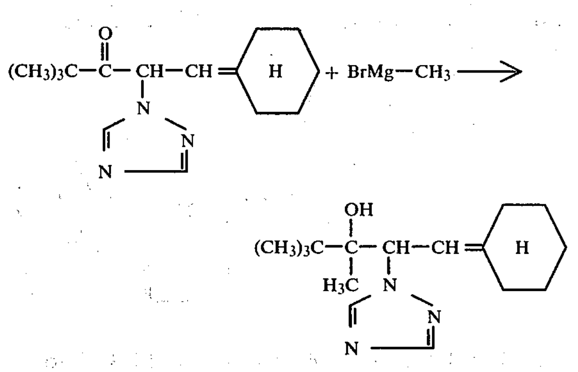

If 1-cyclohexylidene-4,4-dimethyl-1-(1,2,4-triazol-1-yl)-pentan-3-ol, sodium hydride and ethyl bromide are used as starting materials in process variant (c), the course of the reaction can be represented by the following equation:

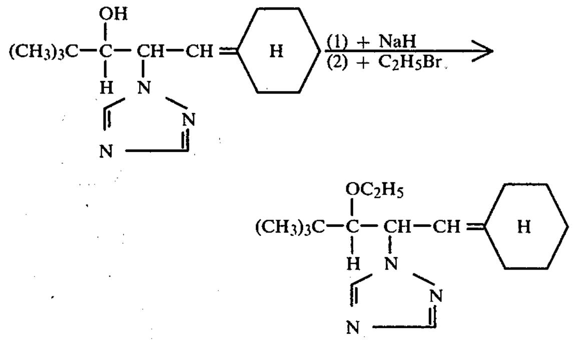

If 1-cyclohexylidene-4,4-dimethyl-2-(1,2,4-triazol-1-yl)-pentan-3-ol, sodium hydride and acetyl chloride are used as starting materials in process variant (c), the course of the reaction can be represented by the following equation:

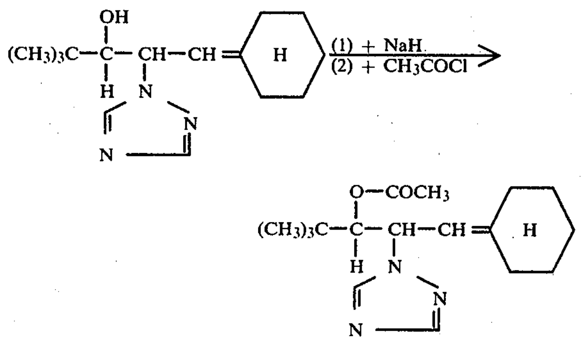

If 1-cyclohexylidene-4,4-dimethyl-2-(1,2,4-triazol-1-yl)-pentan-3-ol and acetic anhydride are used as starting materials in process varient (d), the course of the reaction can be represented by the following equation:

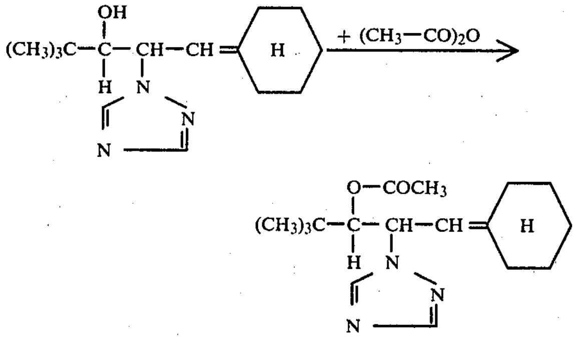

If 1-cyclohexylidene-4,4-dimethyl-2-(1,2,4-triazol-1-yl)-pentan-3-ol and phenyl isocyanate are used as starting materials in process variant (e), the course of the reaction can be represented by the following equation:

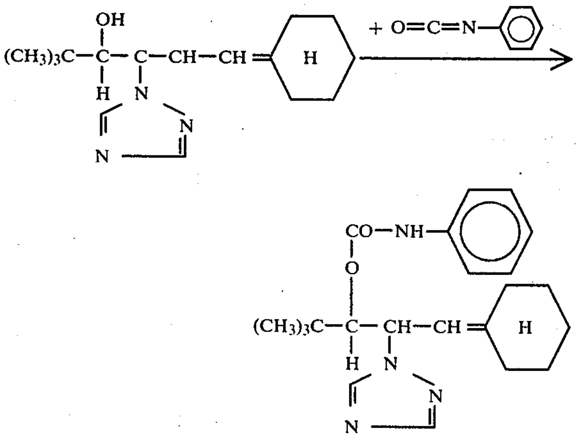

If 2,2,6-trimethyl-4-(1,2,4-triazol-1-yl)-1-hepten-3-one, sodium hydride and 2-chlorobenzyl bromide are used as starting materials in process variant (f), the course of the reaction can be represented by the following equation:

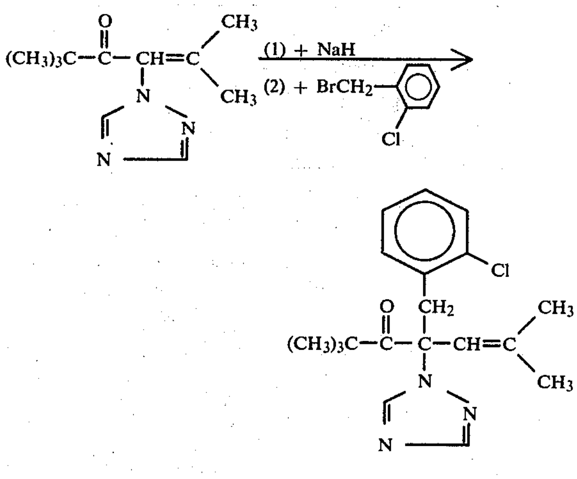

The formula (II) provides a general definition of the triazole-ketones required as starting materials in carrying out process variant (a). In this formula, $R^1$ preferably has those meanings which have already been mentioned as preferred in connection with the description of the substances of the formula (I).

Triazole-ketones of the formula (II) are known (see DE-OS (German Published Specification) No. 2,431,407, DE-OS (German Published Specification) No. 2,610,022 and DE-OS (German Published Specification) No. 2,638,470). They are obtained by reacting the corresponding halogeno-ketones with 1,2,4-triazole in the presence of an acid-binding agent. The compounds in the following table may be mentioned as examples:

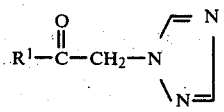
(II)

The formula (III) provides a general definition of the aldehydes also to be used as starting materials for process variant (a). In this formula, $R^2$ and $R^3$ preferably have those meanings which have already been mentioned as preferred in connection with the description of the substances of the formula (I).

The aldehydes of the formula (III) are generally known compounds of organic chemistry. The following compounds may be mentioned as examples:

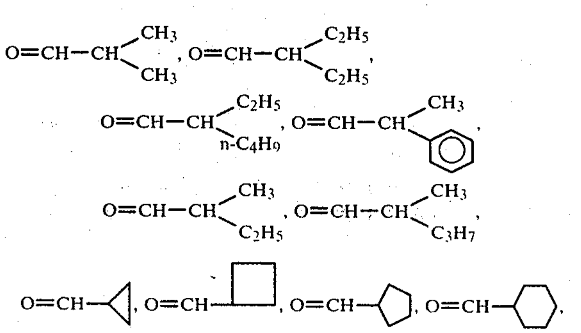

-continued

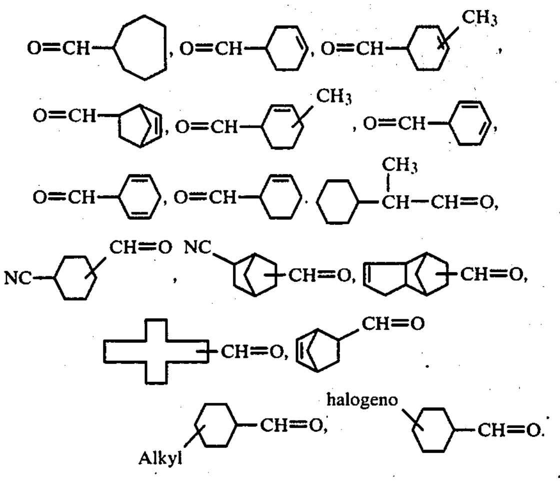

The formula (Ia) provides a general definition of the compounds to be used as starting materials for process variants (b) and (f). In this formula, $R^1$, $R^2$ and $R^3$ preferably have those meanings which have already been mentioned as preferred in connection with the description of the substances of the formula (I).

The complex hydrides also required for process variant (b)($\alpha$) are generally known compounds of organic chemistry. Preferred examples which may be mentioned are sodium borohydride, sodium cyanoborohydride and lithium alanate.

The formula (IV) provides a general definition of the Grignard compounds also to be used as starting materials for process (b)($\beta$). In this formula, $R^6$ preferably has those meanings which have already been mentioned as preferred for $R^5$, insofar as it represents alkyl or optionally substituted aralkyl, in connection with the description of the substances of the formula (I). Hal preferably represents chlorine, bromide or iodine.

The Grignard compounds of the formula (IV) are generally known compounds of organic chemistry. Examples which may be mentioned are methyl-magnesium bromide, ethyl-magnesium bromide, isopropyl-magnesium bromide and benzyl-magnesium bromide.

The formula (Ib) provides a general definition of the substances according to the invention, to be used as starting materials for process variants (c), (d) and (e). In this formula, $R^1$, $R^2$, $R^3$ and $R^5$ preferably have those meanings which have already been mentioned as preferred in connection with the description of the substances of the formula (I).

The formula (V) provides a general definition of the halides also to be used as starting materials for process variant (c). In this formula, $R^7$ preferably has those meanings which have already been mentioned as preferred for $R^4$, insofar as it represents alkyl, optionally substituted aralkyl, acyl or carbamoyl, in connection with the description of the substances of the formula (I). Hal preferably represents fluorine, chlorine or bromine.

The halides of the formula (V) are generally known compounds of organic chemistry.

The formula (VI) provides a general definition of the acid anhydrides also to be used as starting materials for process variant (d). In this formula, $R^8$ preferably has those meanings which have already been mentioned as preferred for $R^4$, insofar as it represents acyl, in connection with the description of the substances of the formula (I).

The acid anhydrides of the formula (VI) are generally known compounds of organic chemistry.

The formula (VII) provides a general definition of the isocyanates also to be used as starting materials for process variant (e). In this formula, $R^9$ preferably has those meanings which have already been mentioned as preferred for $R^{12}$, insofar as it represents alkyl, halogenoalkyl or optionally substituted aryl, in connection with the description of the substances of the formula (I).

The isocyanates of the formula (VII) are generally known compounds of organic chemistry.

The formula (VIII) provides a general definition of the halides also to be used as starting materials for process variant (f). In this formula, Y preferably has those meanings which have already been mentioned as preferred for R, insofar as it represents alkyl or optionally substituted aralkyl, in connection with the description of the substances of the formula (I). Hal preferably represents fluorine, chlorine or bromine.

The halides of the formula (VIII) are generally known compounds of organic chemistry.

Preferred solvents for process variant (a) are inert organic solvents. These include, as preferences, alcohols, such as methanol and ethanol; ethers, such as tetrahydrofuran and dioxane; aliphatic and cycloaliphatic hydrocarbons, such as hexane and cyclohexane; aromatic hydrocarbons, such as benzene, toluene and cumene; or halogenated aliphatic and aromatic hydrocarbons, such as methylene chloride, carbon tetrachloride, chloroform, chlorobenzene and dichlorobenzene.

Process variant (a) is carried out in the presence of a catalyst. It is possible to employ any of the acid and, especially, basic catalysts, and buffer mixtures thereof, which can customarily be used. These catalysts include, as preferences, Lewis acids, for example boron trifluoride, boron trichloride, tin tetrachloride or titanium tetrachloride; and organic bases, such as pyridine and piperidine; and, especially, piperidine acetate.

The reaction temperatures can be varied within a substantial range in carrying out process variant (a). In general, the reaction is carried out at from 20° to 160° C., preferably at the boiling point of the particular solvent.

In carrying out process variant (a), 1 to 1.5 mols of aldehyde of the formula (III) and catalytic to 0.2 molar amounts of catalysts are generally employed per mol of triazole-ketone of the formula (II). To isolate the compounds of the formula (I), the desired product is isolated by customary methods, for example by salt formation (see the preparative examples) or by working up by chromatography. An unambiguous characterization is effected on the basis of spectroscopic data, especially the NMR spectra.

Preferred solvents for process variant (b)($\alpha$) are polar organic solvents. These include, as preferences, alcohols, such as methanol, ethanol, isopropanol or butanol;

ethers, such as diethyl ether or tetrahydrofuran; and, if appropriate, aqueous solutions thereof.

The reaction temperatures can be varied within a substantial range in carrying out process variant (b)($\alpha$). In general, the reaction is carried out at from 0° to 30° C., preferably at from 0° to 20° C.

Process variant (b)($\alpha$) is preferably carried out using equimolar amounts of the reactants, or using an excess of reducing agent. To isolate the compound of the formula (I), the reaction mixture is taken up in dilute hydrochloric acid and extracted with an organic solvent. Further working up is effected in the customary manner.

Preferred solvents for process variant (b)($\beta$) are ethers, such as diethyl ether, dibutyl ether and tetrahydrofuran.

The reaction temperatures can be varied within a substantial range in carrying out process variant (b)($\beta$). In general, the reaction is carried out at from 0° to 80° C., preferably from 30° to 60° C.

In carrying out process variant (b)($\beta$), 2 to 3 mols of Grignard compound are employed per mol of the compound of the formula (Ia). The compound of the formula (I) is isolated in a customary and generally known manner.

Preferred solvents for process variant (c) are inert organic solvents. These include, as preferences, ethers, such as diethyl ether and dioxane; aromatic hydrocarbons, such as toluene and benzene (and in some cases, also chlorinated hydrocarbons, such as chloroform, methylene chloride or carbon tetrachloride); ketones, such as acetone or methyl ethyl ketone; and nitriles, such as acetonitrile. For reasons of simplicity, an acid halide employed can, if appropriate, also be used as the solvent, whereupon an appropriate excess becomes necessary.

The reaction temperatures can be varied within a substantial range in carrying out process variant (c). In general, the reaction is carried out at from 20° to 150° C., preferably from 20° to 100° C., or at the boiling point of the particular solvent.

If appropriate, process variant (c) can be carried out in the presence of a strong base. Preferred strong bases include alkali metal hydrides, alkali metal amides and alkali metal alcoholates, for example sodium hydride, sodium amide and potassium tert.-butylate.

If appropriate, process variant (c) can be carried out in the presence of an acid-binding agent (hydrogen halide acceptor). Suitable acid-binding agents include organic bases, preferably tertiary amines, for example triethylamine; and furthermore inorganic bases, for example alkali metal hydroxides and alkali metal carbonates.

In carrying out process variant (c), 1 to 3 mols of halide of the formula (V) are preferably employed per mol of the compound of the formula (Ib). To isolate the end product, the reaction mixture is freed from solvent, and water and an organic solvent are added to the residue. The organic phase is separated off and worked up in the customary manner.

In a preferred embodiment, a procedure is appropriately followed in which a compound of the formula (Ib) is used as the starting compound, this compound is converted into the alkenolate by means of an alkali metal hydride or alkali metal amide in a suitable inert organic solvent, and the alkenolate is reacted immediately, without isolation, with a halide of the formula (V), the compounds of the formula (I) being obtained in one operation with elimination of an alkali metal halide.

According to another preferred embodiment, the reaction of halides of the formula (V), in which $R^7$ represents alkyl or optionally substituted aralkyl, in the above-mentioned preferred embodiment is carried out in a two-phase system, for example aqueous sodium hydroxide solution or potassium hydroxide solution/-toluene or methylene chloride, with the addition of 0.01–1 mol of a phase transfer catalyst, for example an ammonium or phosphonium compound, benzyl-dodecyl-dimethyl-ammonium chloride and triethyl-benzyl-ammonium chloride being mentioned as examples.

Preferred solvents for process variant (d) are inert organic solvents. These include, as preferences, the solvents listed in the case of process variant (c) and the particular acid anhydrides of the formula (VI) used.

Preferred catalysts which can be used in process variant (d) are any of the customary acid and basic catalysts, for example sulphuric acid, hydrogen chloride, hydrogen bromide, boron trifluoride, zinc chloride, sodium acetate, sodium benzoate, sodium carbonate, calcium oxide, magnesium oxide, pyridine and triethylamine.

The reaction temperatures can be varied within a substantial range in carrying out process variant (d). In general, the reaction is carried out at from 20° to 150° C., preferably from 50° to 120° C.

Equimolar amounts of the reactants are preferably used in carrying out process variant (d). For reasons of simplicity, the acid anhydride of the formula (VI) employed can also be used as the solvent, whereupon an appropriate excess becomes necessary. The compound of the formula (I) is isolated in the customary manner.

Preferred solvents for process variant (e) are inert organic solvents. These include, as preferences, the solvents listed in the case of process variant (c).

Preferred catalysts which can be used in process variant (e) are tertiary bases, such as triethylamine and pyridine, or organo-tin compounds, such as dibutyl-tin dilaurate and tributyl-tin laurate.

The reaction temperatures can be varied within a substantial range in carrying out process variant (e). In general, the reaction is carried out at from 0° to 100° C., preferably from 20° to 40° C.

Equimolar amounts of the reactants are preferably used for carrying out process variant (e). To isolate the compound of the formula (I), the solvent is distilled off and the residue is worked up by customary methods.

Preferred solvents for process variant (f) are inert organic solvents. These include, as preferences, ethers, such as diethyl ether and dioxane; aromatic hydrocarbons, such as toluene and benzene; and, especially, dimethylformamide.

The reaction temperatures can be varied within a substantial range in carrying out process variant (f). In general, the reaction is carried out at from 20° to 150° C., preferably from 20° to 100° C.

Process variant (f) is carried out in the presence of a strong base. Preferred strong bases include alkali metal hydrides and alkali metal amides, for example sodium hydride and sodium amide.

In carrying out process variant (f), 1 to 3 mols of halide of the formula (VIII) are preferably employed per mol of the compound of the formula (Ia). The compounds of the formula (I) are isolated in the customary and generally known manner.

The compounds of the formula (I) which can be prepared by process variants (a) to (f) can be converted into acid addition salts or metal salt complexes. Of course, the physiologically acceptable salts and complexes are preferred.

The following acids can preferably be used for the preparation of physiologically acceptable acid addition salts of the compounds of the formula (I): the hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid), and sulphonic acids (for example p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII can preferably be used for the preparation of metal salt complexes of the compounds of the formula (I), examples of preferred metals which may be mentioned being copper, zinc, manganese, magnesium, tin, iron and nickel.

Preferred anions of the salts are those which are derived from the following acids: hydrogen halide acids (for example hydrochloric acid and hydrobromic acid), phosphoric acid, nitric acid and sulphuric acid.

Metal-salt complexes of compounds of the formula (I) can be obtained in a simple manner by customary processes, for example by dissolving the metal salt in alcohol, for example ethanol, and adding the solution to the compound of the formula (I). The metal salt complexes can be purified in a known manner, for example by filtration, isolation and if appropriate by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds which can be used according to the invention can be employed with particularly good success for combating those fungi which cause powdery mildew diseases, especially for combating Erysiphe species, for example the powdery mildew of barley or cereal causative organism (*Erysiphe graminis*).

It should be particularly emphasized that the active compounds according to the invention not only develop a protective action, but also have a systemic action. Thus, it is possible to protect plants against fungal attack when the active compound is fed to the above-ground parts of the plant via the soil and the root or via the seed.

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at borders. The inhibition of growth of herbaceous and woody plants at borders and in the vicinity of overland pipelines or, quite generally, in areas in which heavy growth is undesired, is also of importance.

The use of growth regulators to inhibit the growth in height of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegetative growth permits denser planting of the crop, so that a greater yield per area of ground can be achieved.

A further mechanism of increasing the yield by means of growth inhibitors is based on the fact that the nutrients benefit blossoming and fruit formation to a greater extent, while vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favorably to influence the production of the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit—for example in the case of table fruit—in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted into the customary formulations, such as solutions, emulsions, powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the fungicidal treatment of parts of plants, the active compound concentrations in the use forms can be varied within a substantial range. They are, in general, from 1 to 0.0001% by weight, preferably from 0.5 to 0.001%.

In the treatment of seed, amounts of active compound of 0.001 to 50 g, especially 0.01 to 10 g, are generally required per kilogram of seed.

For the treatment of soil, active compound concentrations of 0.00001 to 0.1% by weight, especially 0.0001 to 0.02%, are generally required at the place of action.

When the active compounds are used as plant growth regulators, the active compound concentrations can be varied within a substantial range. In general, 0.01 to 50 kg, preferably 0.05 to 10 kg, of the active compound are used per hectare of soil surface.

The present invention also provides plant-growth regulating of fungicidal compositions containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is illustrated in the following examples:

EXAMPLE 1

(a) 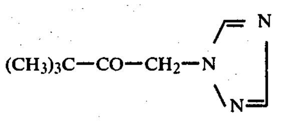

138 g (2 mol) of 1,2,4-triazole were added in portions to 276.4 g (2 mol) of ground potassium carbonate and 269.2 g (2 mol) of α-chloropinacolin in 500 ml of acetone at room temperature, during which the internal temperature rose to the boiling point. The reaction mixture was stirred under reflux for 5 hours and then cooled to room temperature. It was filtered and the filtrate was concentrated by distilling off the solvent in vacuo. After adding benzine, the oily residue crystallized. 240.8 g (72% of theory) of 3,3-dimethyl-1-(1,2,4-triazol-1-yl)-butan-2-one of melting point 62°-64° C. were obtained.

(b) 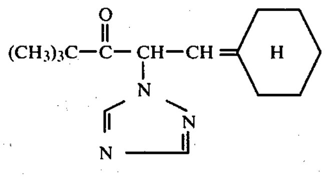 (1)

Process variant (a)

83.5 g (0.5 mol) of pinacolyltriazole, 60 g (0.54 mol) of cyclohexanecarbaldehyde, 4.2 g (0.05 mol) of piperidine and 6 g (0.1 mol) of glacial acetic acid in 300 ml of toluene were heated under reflux, using a water separator, until no further water was separated off. The cooled reaction solution was washed with saturated sodium chloride solution, dried and filtered and the filtrate was concentrated on a rotary evaporator.

The residue was taken up in 500 ml of acetone, and a filtered solution of 90 g (0.25 mol) of naphthalene-1,5-disulphonic acid was added, while stirring.

The precipitate which thereby separated out was filtered off, washed with acetone and suspended in 500 ml of methylene chloride. Half-concentrated sodium carbonate solution was then added until the reaction was alkaline, the organic phase was separated off, washed with water, dried and filtered and the filtrate was concentrated on a rotary evaporator.

49 g (38.0% of theory) of 1-cyclohexylidene-4,4-dimethyl-2-(1,2,4-triazol-1-yl)-pentan-3-one were obtained as a yellowish oil of refractive index $n_D^{20}$: 1.4990.

EXAMPLE 2

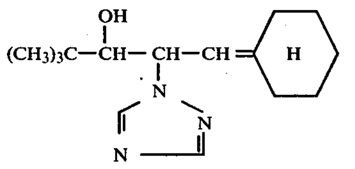

(2)

Process variant (b)(α)

52 g (0.2 mol) of 1-cyclohexylidene-4,4-dimethyl-2-(1,2,4-triazol 1-yl)-pentan-3-one (Example 1) were dissolved in 300 ml of methanol, and 8.5 g of sodium borohydride were added in portions, while stirring and cooling. When the reaction had ended, the solution was brought to pH 6 and concentrated on a rotary evaporator. The residue was taken up in 200 ml of methylene chloride, the methylene chloride mixture was washed with saturated sodium bicarbonate solution, dried and filtered and the filtrate was concentrated on a rotary evaporator. The oily residue was purified over a column (chloroform: methanol=2:1).

33.7 (64% of theory) of 1-cyclohexylidene-4,4-dimethyl-2-(1,2,4-triazol-1-yl)-pentan-3-ol were obtained as a colorless oil of refractive index $n_D^{20}$: 1.4993.

EXAMPLE 3

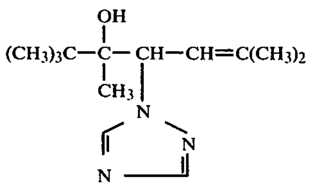

(3)

Process variant (b)(β)

A solution of methyl-magnesium iodide, prepared from 69 g (0.5 mol) of methyl iodide and 10 g (0.42 mol) of magnesium in 150 ml of ether, was slowly added dropwise to a solution of 44 g (0.2 mol) of 2,2,6-trimethyl-4-(1,2,4-triazol-1-yl)-5-hepten-3-one (preparation analogous to Example 1) in 150 ml of ether, while cooling, and the mixture was then heated under reflux for 1 hour. The reaction mixture was poured onto an aqueous ammonium chloride solution and the ether phase was separated off. The aqueous phase was extracted again with ether, the combined ether phases were washed with water and dried over sodium sulphate and the solvent was stripped off. 0.05 mol of naphthalene-1,5-disulphonic acid in 100 ml of acetone was added to the residue and the precipitate which had separated out was filtered off (23.1 g). The precipitate was suspended in 200 ml of water, 8.4 g (0.1 mol) of sodium bicarbonate were added and the precipitate was filtered off.

The solid recrystallized from cyclohexane. 11.2 g (23.2% of theory) of 2,2,3,6-tetramethyl-4-(1,2,4-triazol-1-yl)-5-hepten-3-ol of melting point 115°–116° C. were obtained.

EXAMPLE 4

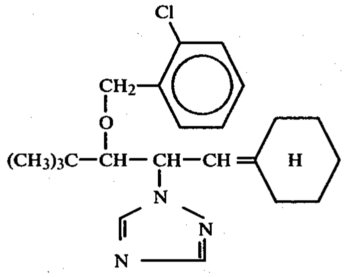

(4)

Process variant (c)

A solution of 13.1 g (0.15 mol) of 1-cyclohexylidene-4,4-dimethyl-2-(1,2,4-triazol-1-yl)-pentan-3-ol (Example 2) in 50 ml of dioxane was added dropwise to a suspension of 2.0 g of 80% strength sodium hydride in 50 ml of dioxane and the mixture was then warmed to 65° C. for 45 minutes. After cooling, 10.0 g (0.06 mol) of 2-chlorobenzyl chloride were added dropwise and the mixture was heated under reflux overnight. 5 ml of methanol were then added and the reaction was concentrated. The residue was taken up in methylene chloride and the methylene chloride mixture was washed several times with water. The organic phase was dried over sodium sulphate, concentrated and finally degassed under a high vacuum. 14.2 g (72% of theory) of 1-cyclohexylidene-3-(2-chlorobenzyloxy)-4,4-dimethyl-2-(1,2,4-triazol-1-yl)-pentane were obtained as a yellowish oil with a refractive index of $n_D^{20}$=1.5349.

EXAMPLE 5

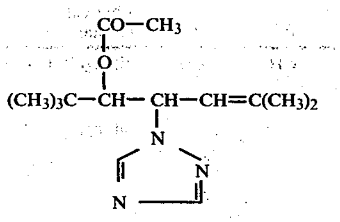

(5)

Process variant (d)

2 ml of pyridine were added to a solution of 11.0 g (0.05 mol) of 2,2,6-trimethyl-4-(1,2,4-triazol-1yl)-5hept-en-3-ol (preparation analogous to Example 2) in 100 ml of acetic anhydride and the mixture was stirred at 70° C. for four hours. Thereafter, the reaction mixture was poured onto water and neutralized with sodium bicarbonate. The aqueous phase was extracted several times with ether and the ether phase was dried over sodium sulphate and concentrated. 9.7 g (74% of theory) of 3-acetoxy-2,2,6-trimethyl-4-(1,2,4-triazol-1-yl)-5-heptene were obtained as a colorless oil with a refractive index of $n_D^{20}=1.4809$.

EXAMPLE 6

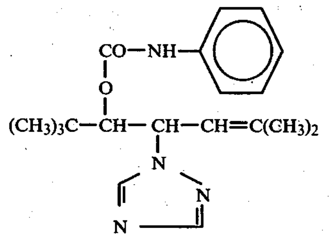

(6)

Process variant (e)

8.33 g (0.07 mol) of phenyl isocyanate and 2 drops of desmorapid were added to a solution of 15.0 g (0.07 mol) of 2,2,6-trimethyl-4-(1,2,4-triazol-1-yl)-5-hepten-3-ol (preparation analogous to Example 2) in 50 ml of methylene chloride and the mixture was heated under reflux for 5 hours. After stripping off the solvent, the residue was stirred with ether and the precipitate which had separated out was filtered off. 3.0 g (38% of theory) of 3-phenyl-carbamoyloxy-2,2,6-trimethyl-4-(1,2,4-triazol-1-yl)-5-heptene of melting point 185°-187° C. were obtained.

EXAMPLE 7

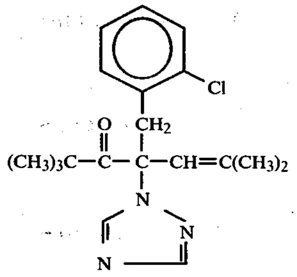

(7)

Process variant (f)

44 g (0.2 mol) of 2,2,6-trimethyl-4-(1,2,4-triazol-1-yl)-5-hepten-3-one (preparation analogous to Example 1), dissolved in 40 ml of dimethylformamide, were added dropwise to a suspension of 6 g of sodium hydride in 60 ml of dimethylformamide and the mixture was then subsequently stirred at room temperature for 1 hour. 32.2 g (0.2 mol) of 2-chlorobenzyl chloride were then added dropwise (slightly exothermic reaction) and the reaction mixture was stirred at room temperature overnight. Thereafter, the solution was poured onto water and acidified with acetic acid. The aqueous phase was extracted several times with 50 ml of methylene chloride each time and the organic phase was washed with water, dried over sodium sulphate and concentrated by distilling off the solvent. 28 g (40% of theory) of 4-(2-2,2,6-trimethyl-4-(1,2,4-triazol-1yl)-5-hepten-3-one of melting point 115°-116° C. were obtained.

The following compounds of the general formula

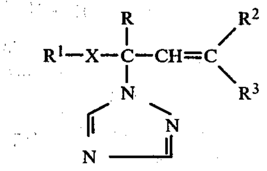

(I)

were obtained by procedures analogous to those of Examples 1 to 7.

| Compound No. | $R^1$ | X | R | $R^2$ | $R^3$ | Physical constant |
|---|---|---|---|---|---|---|
| 8 | $(CH_3)_3C$ | —CO— | H | $CH_3$ | $CH_3$ | boiling point: 98-100° C./0.1 mmHg |
| 9 | $(CH_3)_3C$ | —CO— | H | 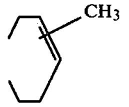 | | oil |
| 10 | $(CH_3)_3C$ | —CO— | H | 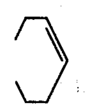 | | melting point: 42° C. |
| 11 | $(CH_3)_3C$ | —CO— | H | $C_2H_5$ | $C_2H_5$ | boiling point: 105° C./0.1 mmHg |

-continued

| Compound No. | $R^1$ | X | R | $R^2$ | $R^3$ | Physical constant |
|---|---|---|---|---|---|---|
| 12 | $(CH_3)_3C$ | —CO— | 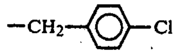 | $CH_3$ | $CH_3$ | oil, $n_D^{20}$: 1.5424 |
| 13 | $(CH_3)_3C$ | —CH(OH)— | H | 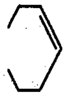 | | oil, $n_D^{20}$: 1.5210 |
| 14 | $(CH_3)_3C$ | —CH(OH)— | H | 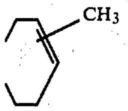 | | melting point: 138° C. ($xH_2SO_4$) |
| 15 | $(CH_3)_3C$ | —CH(OH)— | H | 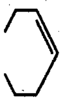 | | melting point: 153° C. ($xH_2SO_4$) |
| 16 | $(CH_3)_3C$ | —CH(OH)— | 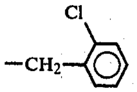 | $CH_3$ | $CH_3$ | oil, $n_D^{20}$: 1.5394 |
| 17 | $(CH_3)_3C$ | 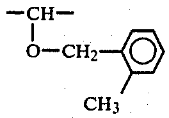 | H | 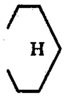 | | oil, $n_D^{20}$: 1.5304 |
| 18 | $(CH_3)_3C$ | 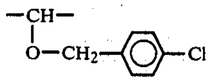 | H | $CH_3$ | $CH_3$ | melting point: 150° C. |
| 19 | $(CH_3)_3C$ | 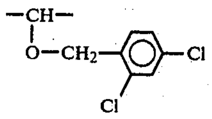 | H | $CH_3$ | $CH_3$ | boiling point: 150° C./0.1 mmHg |
| 20 | $(CH_3)_3C$ | 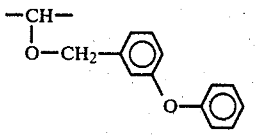 | H | $CH_3$ | $CH_3$ | boiling point: 150° C./0.1 mmHg |
| 21 | $(CH_3)_3C$ | 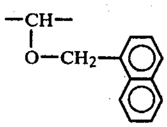 | H | $CH_3$ | $CH_3$ | boiling point: 140° C./0.1 mmHg |
| 22 | $(CH_3)_3C$ | 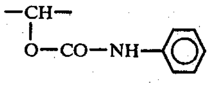 | H | 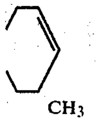 | | melting point: 159° C. |
| 23 | $(CH_3)_3C$ | 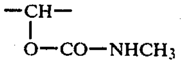 | H | $CH_3$ | $CH_3$ | melting point: 178° C. |
| 24 | $(CH_3)_3C$ | —CH(OH)— | H | $CH_3$ | $CH_3$ | boiling point: 150° C./0.1 mmHg |
| 25 | $(CH_3)_3C$ | —CO— | H | $CH_3$ | 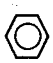 | oil |
| 26 | $ClCH_2—C(CH_3)_2—$ | —CO— | H | $CH_3$ | $C_2H_5$ | oil |
| 27 | $ClCH_2—C(CH_3)_2—$ | —CH(OH)— | H | $CH_3$ | $C_2H_5$ | oil |
| 28 | $ClCH_2—C(CH_3)_2—$ | —CH(OH)— | H | $CH_3$ | 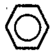 | oil |
| 29 | $ClCH_2—C(CH_3)_2—$ | —CO— | H | $CH_3$ | 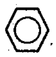 | oil |
| 30 | $(CH_3)_3C$ | —CH(OH)— | H | $CH_3$ | 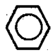 | $n_D^{20}$: 1,5427 |

The plant-growth regulating and fungicidal activity of the compounds of this invention is illustrated by the following examples wherein the compounds according to the present invention are each identified by the number (given in brackets) from Examples 1 to 7 and the table hereinabove:

The known comparison compounds are identified as follows:

(A) =
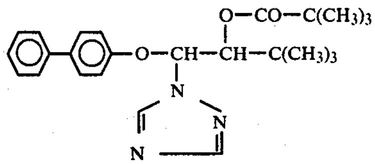

(B) =
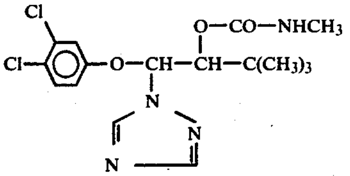

(C) =
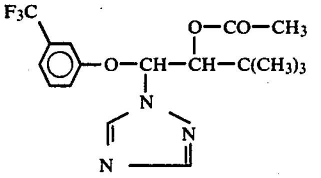

(D) =
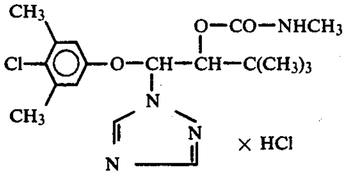

(E) =
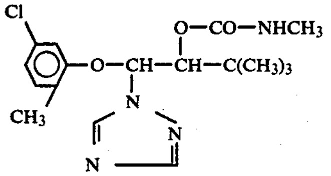

(F) =
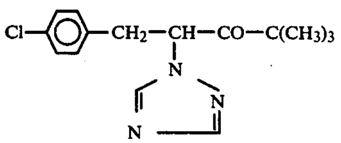

(G) =
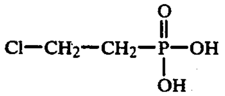

[2-chloroethylphosphonic acid]

(H) = $Cl-CH_2-CH_2-\overset{\oplus}{N}(CH_3)_3Cl^{\ominus}$

[2-chloroethyl-trimethyl-ammonium chloride]

EXAMPLE 8

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis var. hordei.*

After 6 days' dwell time of the plants at a temperature of 21-22 deg. C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

In this test, for example, the following compounds showed a very good action which was superior to that of the compounds (A), (B) and (C) known from the prior art: compounds (13), (14), (15), (4), (17), (2), (24), (23), (18), (19), (20), (21), (7) and (3).

EXAMPLE 9

Powdery mildew of barley (*Erysiphe graminis var. hordei*) (fungal disease of cereal shoots)/systemic The active compound was used as a pulverulant seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis var. hordei* and grown on at 21-22 deg. C. and 80-90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The more active the compound, the lower was the degree of mildew infection.

In this test, for example, the following compounds showed a very good action which was superior to that of the compounds (B), (D) and (E) known from the prior art: compounds (13), (15), (2), (8), (24), (18), (5) and (3).

EXAMPLE 10

Mycelium growth test

Nutrient medium used:

20 parts by weight of agar-agar
200 parts by weight of potato decoction
5 parts by weight of malt
15 parts by weight of dextrose
5 parts by weight of peptone
2 parts by weight of disodium hydrogen phosphate
0.3 part by weight of calcium nitrate Composition of the solvent mixture:

0.19 part by weight of acetone or dimethylformamide
0.01 part by weight of emulsifier (alkylaryl polyglycol ether)
1.80 parts by weight of water Ratio of solvent mixture to nutrient medium:

2 parts by weight of solvent mixture
100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42 deg. C.) and was then poured into Petri dishes of 9 cm diameter. Control plates to which the preparation had not been added were also set up.

When the nutrient medium had cooled and solidified, the plates were inoculated with the species of organisms stated hereinbelow and incubated at about 21 deg. C.

Evaluation was carried out after 4–10 days, dependent upon the speed of growth of the organisms. When evaluation was carried out the radial growth of the organism on the treated nutrient media was compared with the growth on the control nutrient medium. In the evaluation of the organism growth, the following characteristic values were used:

1 no growth
up to 3 very strong inhibition of growth
up to 5 medium inhibition of growth
up to 7 slight inhibition of growth
9 growth equal to that of untreated control.

As test organisms, the following fungi were employed:

In this test, for example, the following compounds showed a very good action which was superior to that of the compound (F) known from the prior art: compounds (18), (7), (13), (14) and (2).

EXAMPLE 11

Influence on growth of sugar-beet

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. In this stage, the plants were sprayed with the preparations of active compound until dripping wet. After 14 days, the additional growth of the plants was measured and the influence on growth in percent of the additional growth of the control plants was calculated. 0% influence on growth denoted a growth which corresponded to that of the control plants. Negative values characterized an inhibition of growth in comparison to the control plants, whereas positive values characterised a promotion of growth in comparison to the control plants.

In this test, active compounds (4), (17), (20), (21) and (23) showed a better influence on growth than the substance (H) known from the prior art.

EXAMPLE 12

Inhibition of growth of soya beans

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Soya bean plants were grown in a greenhouse until the first secondary leaf had unfolded completely. In this stage, the plants were sprayed with the preparations of active compound until dripping wet. After 3 weeks, the additional growth was measured on all the plants and the inhibition of growth in percent of the additional growth of the control plants was calculated. 100% inhibition of growth meant that growth had stopped and 0% denoted a growth corresponding to that of the control plants.

In this test, active compounds (2), (4), (15), (17), (20) and (21) showed a pronounced inhibition of growth in comparison to the control.

EXAMPLE 13

Inhibition of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Cotton plants were grown in a greenhouse until the 5th secondary leaf had unfolded completely. In this stage, the plants were sprayed with the preparations of active compound until dripping wet. After 3 weeks, the additional growth of the plants was measured and the inhibition of growth in percent of the additional growth of the control plants was calculated. 100% inhibition of growth meant that growth had stopped and 0% denoted a growth corresponding to that of the control plants.

In this test, active compounds (2), (14), (17) and (21) showed a pronounced inhibition of growth in comparison to the control.

EXAMPLE 14

Inhibition of growth of barley

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Barley plants were grown in a greenhouse to the 2-leaf stage. In this stage, the plants were sprayed with the preparations of active compound until dripping wet. After 3 weeks, the additional growth was measured on all plants and the inhibition of growth in percent of the additional growth of the control plants was calculated. 100% inhibition of growth meant that growth had stopped and 0% denoted a growth corresponding to that of the control plants.

In this test, active compounds (2) and (21) showed a better inhibition of growth than the substance (G) known from the prior art.

It will be appreciated that the instant specification and examples are set forth by way of illustration and not limitation, and that various modifications and changes may be made without departing from the spirit and scope of the present invention.

What is claimed is:

1. A compound selected from the group consisting of 1-cyclohexylidene-4,4-dimethyl-2-(1,2,4-triazol-1-yl)-pentan-3-ol of the formula

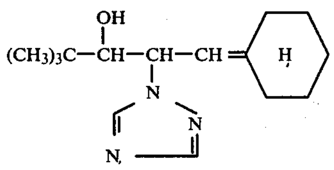

2,2-dimethyl-6-phenyl-4-(1,2,4-triazol-1-yl)-5-hepten-3-ol of the formula

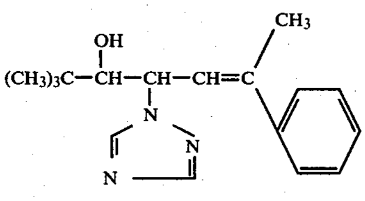

or an acid addition salt or metal salt complex thereof.

2. A compound according to claim 1, in which said compound is 1-cyclohexylidene-4,4-dimethyl-2-(1,2,4-triazol-1-yl)-pentan-3-ol of the formula

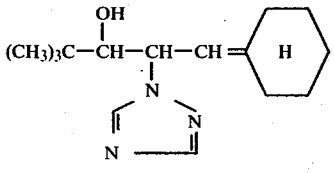

or an acid addition salt or metal salt complex thereof.

3. A compound according to claim 1, in which said compound is 2,2-dimethyl-6-phenyl-4-(1,2,4-triazol-1-yl)-5-hepten-3-ol of the formula

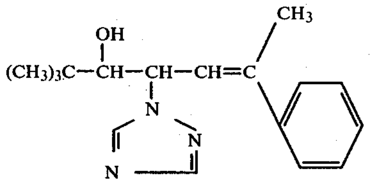

or an acid addition salt or metal salt complex thereof.

4. A fungicidal or plant-growth-regulating composition containing as active ingredient a fungicidally or plant growth regulating effective amount of a compound, acid addition salt or metal salt complex according to claim 1 in admixture with a diluent.

5. A method of combating fungi which comprises applying to fungi, or to a habitat thereof, a fungicidally effective amount of a compound, acid addition salt or metal salt complex according to claim 2.

6. A method of combating fungi which comprises applying to fungi, or to a habitat thereof, a fungicidally effective amount of a compound, acid addition salt or metal salt complex according to claim 3.

7. A method of regulating the growth of plants which comprises applying to the plants, or to a habitat thereof, a plant growth regulating effective amount of a compound, acid addition salt or metal salt complex according to claim 1.

* * * * *

UNITED STATES PATENT AND TRADEMARK OFFICE
CERTIFICATE OF CORRECTION

PATENT NO. : 4,315,764

DATED : February 16, 1982

INVENTOR(S) : Wolf Reiser et al

It is certified that error appears in the above-identified patent and that said Letters Patent are hereby corrected as shown below:

Column 32, between lines 44-45, insert --

| $R^1$ | $R^1$ | $R^1$ |
|---|---|---|
| $-C(CH_3)_3$ | $-CH(CH_3)_2$ | $-CH_3$ |
| $CH_3$<br>$-C-CH_2Cl$<br>$CH_3$ | $CH_3$<br>$-C-CH_2Br$<br>$CH_3$ | $CH_3$<br>$-C-CH_2-F$<br>$CH_3$ |
| $CH_2Cl$<br>$-C-CH_3$<br>$CH_2Cl$ | $CH_3$<br>$CH_3-SO_2-O-CH_2-C-$<br>$CH_3$ | 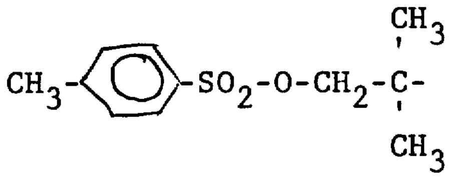 |

UNITED STATES PATENT AND TRADEMARK OFFICE

CERTIFICATE OF CORRECTION

PATENT NO. : 4,315,764

DATED : February 16, 1982

INVENTOR(S) : Wolf Reiser et al

It is certified that error appears in the above-identified patent and that said Letters Patent are hereby corrected as shown below:

$CH_3$ $CH_3-CO-O-CH_2-C$ $CH_3$ $CH_2O-CO-CH$ $CH_3-C-$ $CH_2O-CO-CH_3$

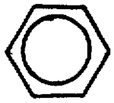

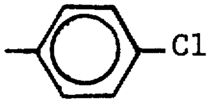

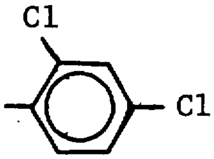

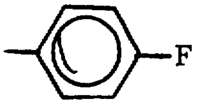

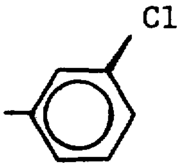

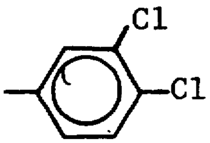

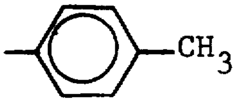

UNITED STATES PATENT AND TRADEMARK OFFICE

CERTIFICATE OF CORRECTION

PATENT NO. : 4,315,764

DATED : February 16, 1982

INVENTOR(S) : Wolf Reiser et al

It is certified that error appears in the above-identified patent and that said Letters Patent are hereby corrected as shown below:

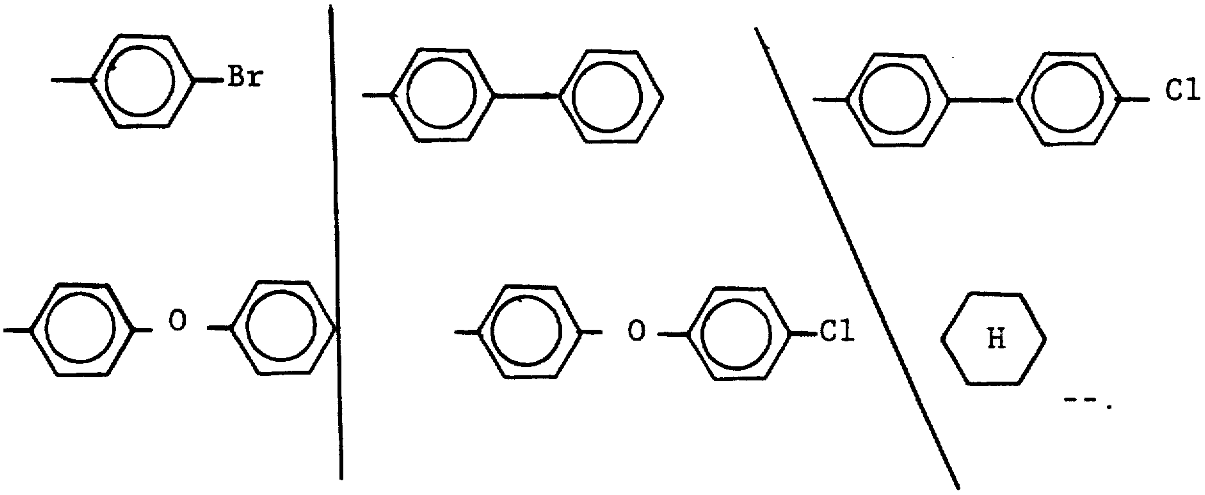

--.

Signed and Sealed this

*Fourth* Day of *January 1983*

[SEAL]

*Attest:*

GERALD J. MOSSINGHOFF

*Attesting Officer* *Commissioner of Patents and Trademarks*